(12) United States Patent
Jaffe et al.

(10) Patent No.: US 8,172,757 B2
(45) Date of Patent: May 8, 2012

(54) METHODS AND DEVICES FOR IMAGE-GUIDED MANIPULATION OR SENSING OR ANATOMIC STRUCTURES

(75) Inventors: Ronen Jaffe, DN Misgav (IL); Bradley H. Strauss, Toronto (CA); Brian K. Courtney, Toronto (CA)

(73) Assignee: Sunnybrook Health Sciences Centre, Toronto (CA)

( * ) Notice: Subject to any disclaimer, the term of this patent is extended or adjusted under 35 U.S.C. 154(b) by 885 days.

(21) Appl. No.: 12/213,386

(22) Filed: Jun. 18, 2008

(65) Prior Publication Data

US 2009/0088648 A1 Apr. 2, 2009

Related U.S. Application Data

(60) Provisional application No. 60/929,187, filed on Jun. 18, 2007.

(51) Int. Cl.
*A61B 8/12* (2006.01)
(52) U.S. Cl. ........ 600/459; 600/437; 600/443; 600/462; 600/466
(58) Field of Classification Search .......... 600/407, 600/437, 443, 459, 462–471, 472, 461, 476, 600/478, 479
See application file for complete search history.

(56) References Cited

U.S. PATENT DOCUMENTS

| | | | |
|---|---|---|---|
| 4,576,177 A | 3/1986 | Webster | |
| 4,898,577 A | 2/1990 | Badger | |
| 5,030,204 A | 7/1991 | Badger | |
| 5,373,849 A | 12/1994 | Maroney et al. | |
| 5,916,210 A | 6/1999 | Winston | |
| 6,004,280 A | 12/1999 | Buck | |
| 6,200,269 B1 * | 3/2001 | Lin et al. | 600/466 |
| 6,390,978 B1 | 5/2002 | Irion et al. | |
| 6,650,923 B1 | 11/2003 | Lesh | |
| 6,755,790 B2 | 6/2004 | Stewart | |
| 6,994,094 B2 | 2/2006 | Schwartz | |
| 7,366,376 B2 | 4/2008 | Shishkov et al. | |
| 7,612,773 B2 * | 11/2009 | Magnin et al. | 345/419 |
| 7,761,139 B2 | 7/2010 | Tearney et al. | |
| 2001/0056232 A1 | 12/2001 | Lardo | |
| 2003/0015037 A1 * | 1/2003 | Stephens et al. | 73/626 |
| 2006/0004062 A1 | 1/2006 | Pei | |

(Continued)

OTHER PUBLICATIONS

Block, P., "Percutaneous Transcatheter Repair for Mitral regurgitation", J. Interventional Card., vol. 19, No. 6, 2006, 547-551 with erratum page vol. 20. No. 1, 2007 pp. 91.

(Continued)

*Primary Examiner* — Tse Chen
*Assistant Examiner* — Mark Remaly

(57) ABSTRACT

Forward-looking ultrasound transducers are positioned at the tip of a transseptal catheter to facilitate transseptal puncture and interventions within the left atrium, pulmonary veins and mitral valve. Catheter devices and systems are guided by forward-looking ultrasound or optical coherence tomography imaging for penetrating from one location within a mammalian patient's body to another location, and/or performing diagnostic or therapeutic interventions. A penetrator, diagnostic, or interventional device (eg. probe, biopsy apparatus, electrode, needle) is positioned at the catheter tip and is advanceable from the catheter to a target location outside of the lumen in which the catheter is positioned. The imaging probe uses forward-looking ultrasound or optical coherence tomography that allows one to locate both the target and the medical device. The operator may then adjust the position and/or rotational orientation of the catheter such that when the medical device is subsequently advanced it will either enter or be deployed at the target location.

40 Claims, 22 Drawing Sheets

U.S. PATENT DOCUMENTS

| | | |
|---|---|---|
| 2006/0241342 A1 | 10/2006 | Macaulay |
| 2008/0177138 A1 | 7/2008 | Courtney et al. |
| 2008/0177139 A1 | 7/2008 | Courtney et al. |
| 2008/0177183 A1 | 7/2008 | Courtney et al. |
| 2008/0243002 A1 | 10/2008 | Munce et al. |
| 2009/0264768 A1 | 10/2009 | Courtney et al. |

OTHER PUBLICATIONS

Haase, J., "Global Cardiovascular Interventions 2006, the XVIIth Frankfurt Course on Cardiovascular Interventions, Dec. 1-2, 2006", J. Interventional Card., vol 19, No. 6, 2006, pp. 483-484.

Lundqvist et al., "Transseptal Left Heart Catheterization: A Review of 278 Studies", Clin. Cardiol, 9, 1986, pp. 21-26.

Roelke et al., "The Technique and Safety of Transseptal Left Heart Catheterization: The Massachusetts General Hospital Experience With 1,279 Procedures", Cather. and Cardio. Diagnosis, 32, 1994, pp. 332-339.

Weiner et al., "Development and Application of Transseptal Left Heart Catheterization", Cather. and Cardio. Diagnosis, 15, 1988, pp. 112-120.

Ross, J., "Considerations Regarding the Technique for Transseptal Left Heart Catheterization", Circulation, 34, 1966, pp. 391-399.

Mitchel et al., "Intracardiac Ultrasound Imaging During Transseptal Catheterization", Chest, 108, 1995, pp. 104-108.

Tucker et al., "Transeophageal Echocardiographic Guidance of Transseptal Left Heart Catheterization During Radiofrequency Ablation of Left-Sided Accessory Pathways in Humans", PACE, vol. 19, Mar. 1996, pp. 272-281.

D. T. Yeh et al., "3-D Ultrasound Imaging Using a Forward-Looking CMUT Ring Array for Intravascular/Intracardiac Applications", IEEE Transactions on Ultrasonics, Ferroelectrics, and Frequency Control 53, 1202-1211 (2006).

F. L. Degertekin et al., "Annular-Ring CMUT Arrays for Forward-Looking IVUS: Transducer Characterization and Imaging", IEEE Transactions on Ultrasonics, Ferroelectrics, and Frequency Control 53, 474-482 (2006).

D. Sahn et al., "Experimental Studies With a 9-French Forward-Looking Intracardiac Imaging and Ablation Catheter Developed in a National Institutes of Health Supported Bioengineering Research Partnership Grant Program", Abstracts from JACC 2007, 8A-9A, 2007.

\* cited by examiner

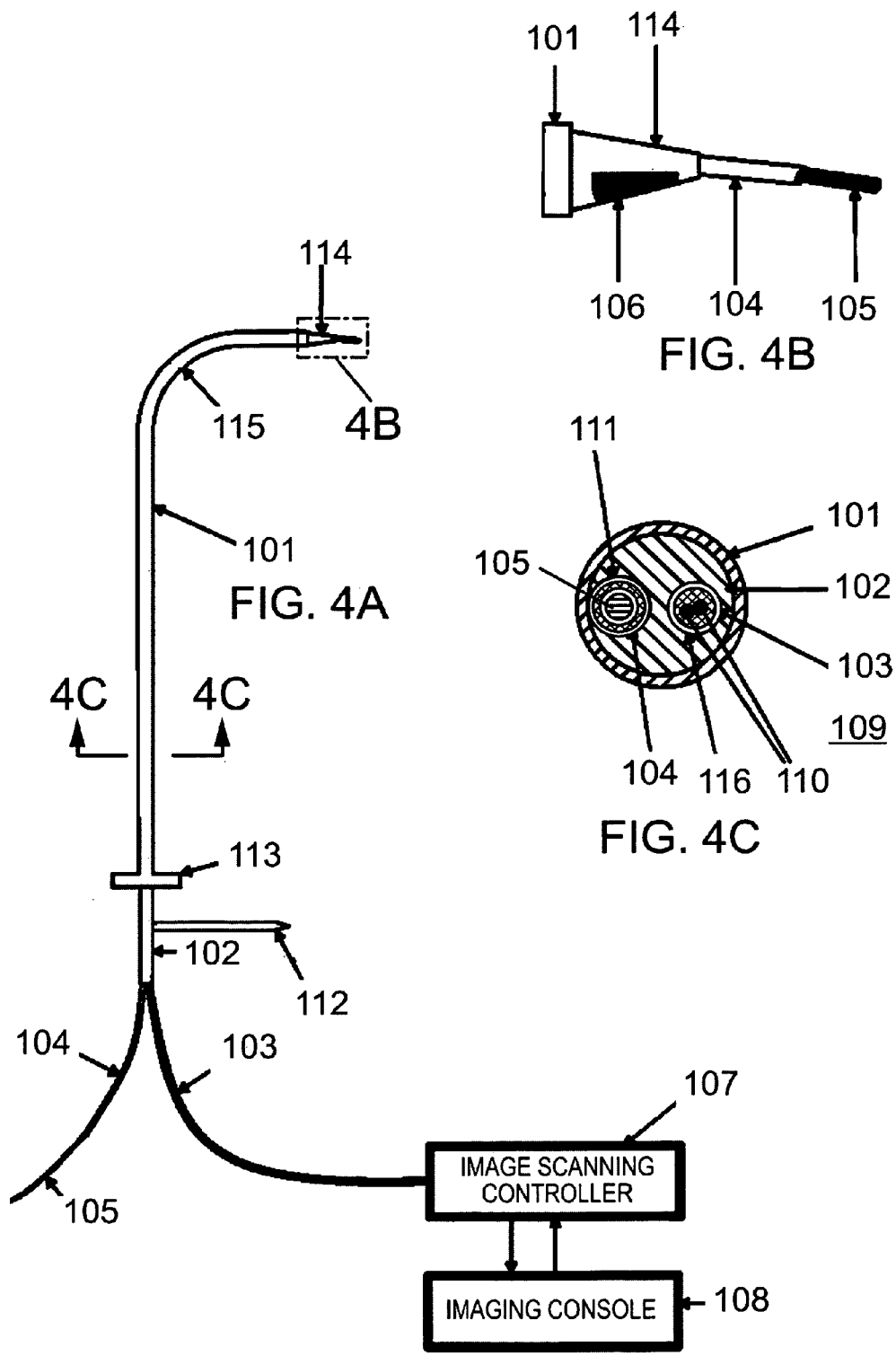

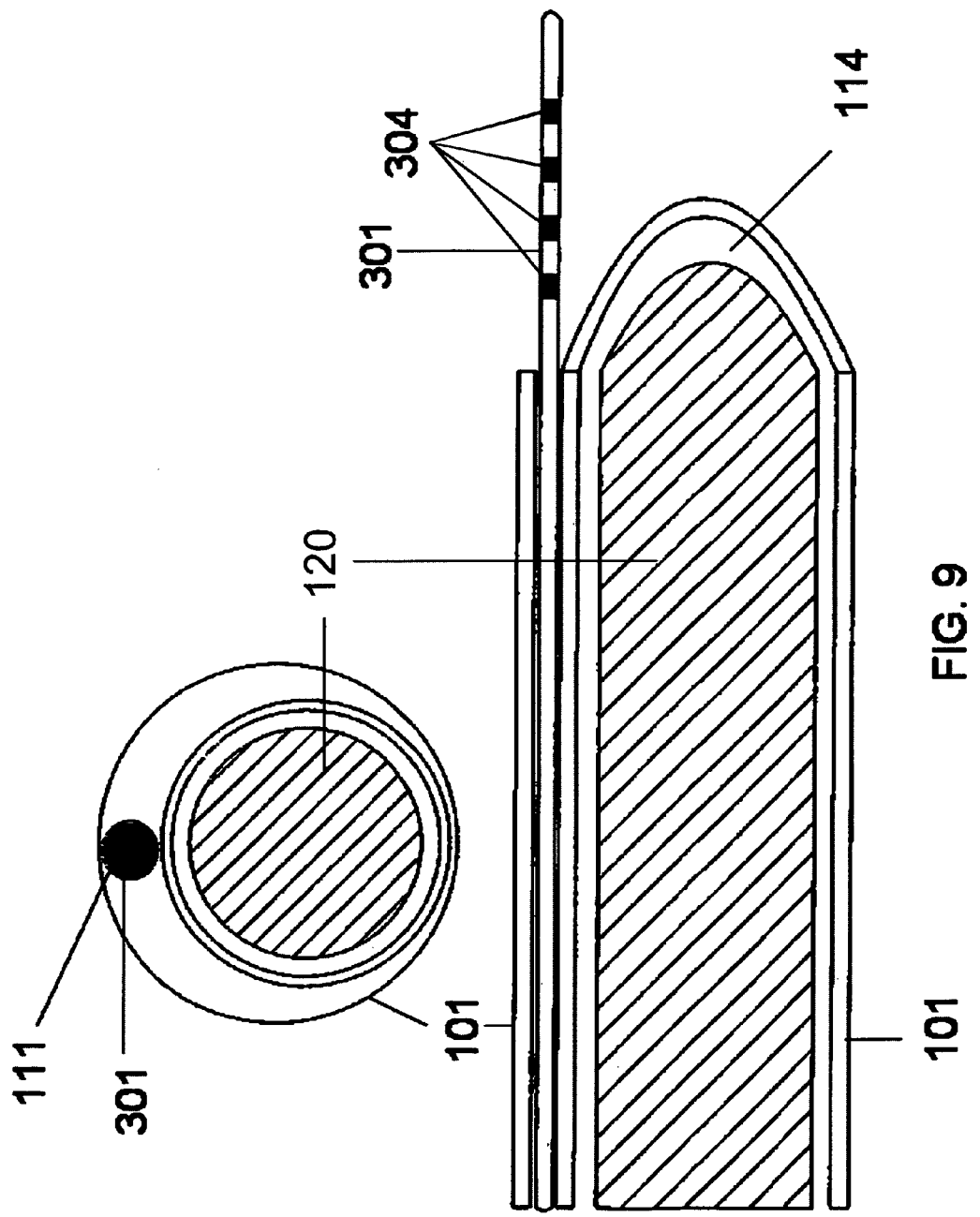

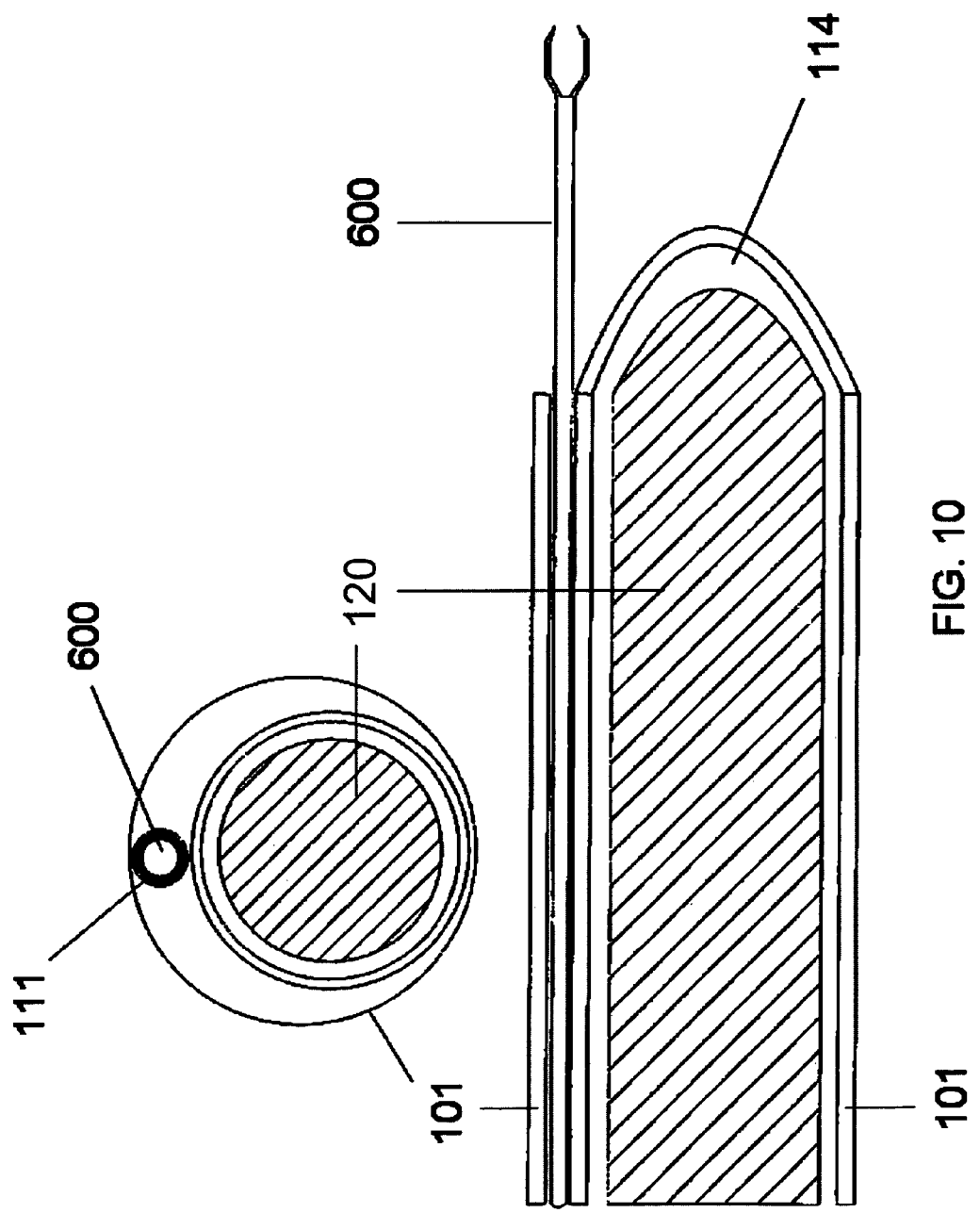

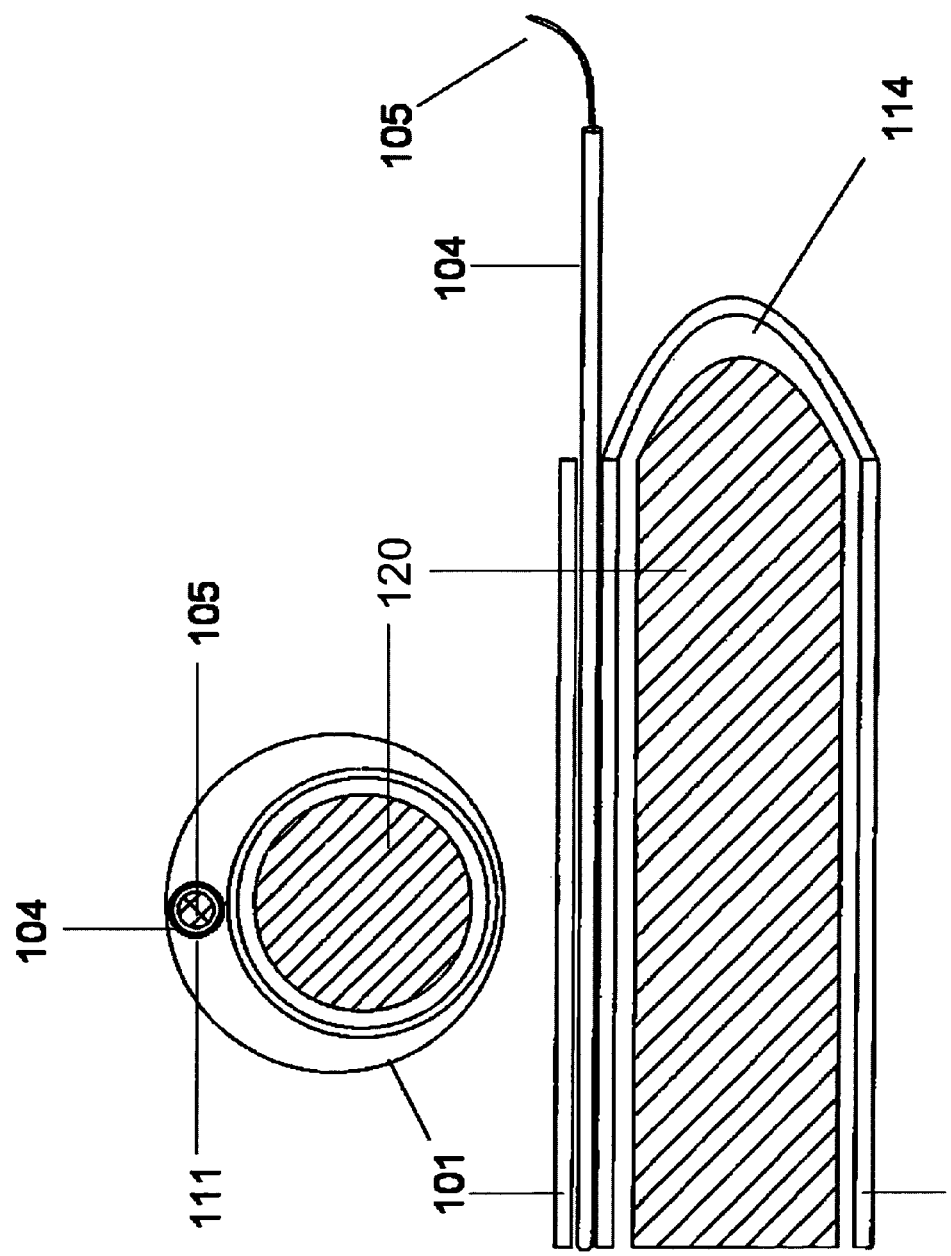

METHODS AND DEVICES FOR IMAGE-GUIDED MANIPULATION OR SENSING OR ANATOMIC STRUCTURES

CROSS REFERENCE TO RELATED U.S. APPLICATIONS

This patent application relates to, and claims the priority benefit from, U.S. Provisional Patent Application Ser. No. 60/929,187 filed on Jun. 18, 2007, in English, entitled METHODS AND DEVICES FOR IMAGE-GUIDED MANIPULATION OR SENSING OF ANATOMIC STRUCTURES, which is incorporated herein by reference in its entirety.

FIELD OF THE INVENTION

The present invention relates to medical devices in the field of minimally invasive medical interventions. In particular, the present invention provides devices and methods for identifying or observing a precise location in the body through and/or upon which medical procedures may be efficiently and safely performed. By way of example, the present invention can be used to identify or observe cardiac tissue during a medical procedure.

BACKGROUND OF THE INVENTION

It may be desired during certain medical procedures to alter anatomic structures, such as by penetrating, or injecting into said structures, by intentionally perforating through these structures or by ablating through them. Such alterations of structure can facilitate diagnostic or therapeutic procedures, but may be accompanied by risks of causing harm to the patient if the alteration occurs in a manner or location other than intended. For example, when many structures are adjacent to each other, and the intention of the medical practitioner is to alter a focal region of these structures, harm can come from unintentionally altering neighboring structures. Image guidance during procedures has the potential to minimize the risk and improve the efficacy of the desired procedure by allowing the medical practitioner to more accurately position and manipulate devices in relation to the anatomic structures of interest.

As an example of a procedure in which image-guided manipulation would be of potential value, we consider the process of crossing the atrial septum of the heart (see J Am Coll Cardiol. 2008; 51:2116-22. Emerging Applications for Transseptal Left Heart Catheterization Old Techniques for New Procedures. Babaliaros V C, Green J T, Lerakis S, Lloyd M, Block P C). The present invention can be adapted to facilitate transseptal access to the left atrium guided by forward-looking ultrasound imaging. Transseptal access is required for performance of a variety of interventional procedures, including repair and/or replacement of diseased mitral and aortic valves, occlusion of the left atrial appendage, ablation of electrical pathways in the left atrium, pulmonary veins and left ventricle for treatment of arrhythmias, repair of defects within the inter-atrial septum, repair of paravalvular leaks and implantation of a percutaneous left ventricular assist device.

Physicians who perform certain invasive cardiology procedures often use minimally invasive techniques to deliver devices from a vein to the right atrium. Once in the right atrium, a variety of catheters may be inserted from the right atrium, through the inter-atrial septum into the left atrium and/or left ventricle. The procedure of crossing the septum typically involves creating a hole within the fossa ovalis through which the device(s) are navigated. Conventionally, a physician uses a transseptal catheter and a long, curved needle for left atrial access from the venous system. The catheter, which is curved to facilitate access to a desired portion of the left-heart anatomy, includes a sheath and may include a separate dilator. The curved needle may be, for example, a stainless steel Brockenbrough curved needle or a trocar. After penetration of the septum with the needle, a wire may be inserted into the left atrial cavity and used as a rail for insertion of larger caliber specific therapeutic or diagnostic devices.

The fossa ovalis is located posterior and caudal to the aortic root, anterior to the free wall of the right atrium, superiorly and posteriorly to the ostium of the coronary sinus and well posterior of the tricuspid annulus and right atrial appendage. The fossa ovalis itself is approximately 2 cm in diameter and is bounded superiorly by a ridge known as the limbus.

Although puncture of the fossa ovalis itself is quite safe, the danger of the transseptal approach lies in the possibility that the needle and catheter will puncture an adjacent structure. Accurate localization of the fossa ovalis and correct positioning of the needle are crucial in order to avoid these structures. After transseptal puncture, the most important problem is to determine whether the tip of the needle is in the left atrium. The most common complication of the transseptal approach is inadvertent puncture of the wall of the heart or great vessels. Puncture can occur in the superior vena cava, free wall of the left or right atria, the left atrial appendage, or the aorta, and can lead to pericardial tamponade and death, (see Cathet Cardiovasc Diagn. 1988; 15(2):112-20; Development and application of transseptal left heart catheterization. Weiner R I, Maranhao V).

Traditionally, transseptal punctures have been guided by fluoroscopy (see Circulation, 1966 September; 34(3):391-9; Considerations regarding the technique for transseptal left heart catheterization, Ross J Jr) however this form of imaging does not accurately delineate the critical cardiac structures; specifically the fossa ovalis. The operator therefore has to rely on a variety of unreliable fluoroscopic landmarks to guide the puncture. Under fluoroscopic guidance, rates of life threatening complications up to 1.2% have been reported (see Cathet Cardiovasc Diagn. 1994 32 332, The technique and safety of transseptal left heart catheterization: the Massachusetts General Hospital experience with 1,279 procedures; Roelke M, Smith A J, Palacios I F; and Clin Cardiol. 1986; 9(1):21-6, Transseptal left heart catheterization: a review of 278 studies; Blomstrom-Lundqvist. Olsson S B, Varnauskas E). Transseptal puncture remains therefore a difficult procedure that is burdened by rare but serious, or even life-threatening complications (see J Invasive Cardiol. 2005 February; 17(2):71-2; Comment on: J. Invasive Cardiol. 2005 February; 17(2): 68-70, Another trick to improve the safety of transseptal puncture; Colombo A, Iakovou I.). Transesophageal and intracardiac echocardiography have been employed to image the septum and atrii, however they have several disadvantages. Transesophageal echocardiography (TEE) limits communication with the patient (as it may require the patient's sedation), and creates risks of esophageal bleeding, longer procedure times, and even inadequate location of the fossa ovalis in some cases (see Roelke CCD 1994 32 332; and Pacing Clin Electrophysiol. 1996 March; 19(3):272-81; Transesophageal echocardiographic guidance of transseptal left heart catheterization during radiofrequency ablation of left-sided accessory pathways in humans. Tucker K J, Curtis A B, Murphy J, Conti J B, Kazakis D J, Geiser E A, Conti C R). Intracardiac echocardiography (ICE) accurately images the fossa ovalis, however it is expensive, invasive and requires placement of an additional device within the heart during the procedure (see Chest. 1995 July; 108(1):104-8; Intracardiac ultrasound imaging during transseptal catheterization; Mitchel J F, Gillam L D, Sanzobrino B W, Hirst J A, McKay R G). ICE may also require an additional access site to the venous system so that the ICE device can be delivered to the right atrium. TEE and ICE are limited by difficulty in imaging the needle tip at the time of the puncture and following penetration, and challenge the operator to coordinate fluoroscopic and ultrasonic images that are acquired from different sources in real-time. Furthermore, most ICE systems are side-viewing and provide only 2D images.

Therefore, transseptal puncture is a complex procedure limited by difficulty in achieving accurate and simultaneous real-time imaging of the needle tip, fossa ovalis and the surrounding cardiac structures. Development of a device that couples forward-looking imaging with the tip of the transseptal catheter would greatly enhance the safety and simplicity of these procedures. Such a device would not only accurately localize the puncture site within the fossa ovalis prior to penetration, but would also confirm the exact localization of the wire tip within the left atrium before insertion of larger caliber devices (with more potential for trauma if inadvertantly placed into an incorrect anatomic space) over the wire.

Following successful transseptal puncture, a variety of subsequent procedures may be performed. Most current transseptal punctures in the U.S. are being performed for the purpose of electrophysiological procedures. Ablation of atrial fibrillation involves isolation of the pulmonary veins using radiofrequency energy (see Circulation 2000 102 2619; Circumferential radiofrequency ablation of pulmonary vein ostia: A new anatomic approach for curing atrial fibrillation; Pappone C, Rosanio S, Oreto G, Tocchi M, Gugliotta F, Vicedomini G, Salvati A, Dicandia C, Mazzone P, Santinelli V, Gulletta S, Chierchia S) or cryoablation. These interventions are associated with prolonged procedure times and high doses of x-ray radiation, primarily because of difficulty in visualizing the ablation targets under fluoroscopy (see Curr Probl Cardiol. 2006 May; 31(5):361-90; Ablation of atrial fibrillation; Riley M J, Marrouche N F). In addition to ablation for atrial fibrillation, transseptal puncture is routine for ablation of accessory pathways located along the mitral annular region, left atrial tachycardias and flutters, and less commonly for variants of atrioventricular nodal reentrant tachycardia. The transseptal route also provides a useful alternative to the retroaortic approach for ablation within the left ventricle and left ventricular outflow tract.

Imaging with intracardiac echocardiography has simplified these procedures (see J Cardiovasc Electrophysiol. 2002 October; 13(10):986-9; Use of intracardiac echocardiography for prediction of chronic pulmonary vein stenosis after ablation of atrial fibrillation; Saad E B, Cole C R, Marrouche N F, Dresing T J, Perez-Lugones A, Saliba W I, Schweikert R A, Klein A, Rodriguez L, Grimm R, Tchou P, Natale A.), however the above limitations apply. Closure of a patent foramen ovale may be enhanced by imaging from transesophageal or intracardiac echocardiography (see Heart. 2005 April; 91(4):444-8; Closure of patent foramen ovale: technique, pitfalls, complications, and follow up; Meier B.) however the same limitations apply. Emerging technologies such as minimally invasive mitral valve repair (see J Interv Cardiol. 2006 December; 19(6):547-51; Erratum in: J Interv Cardiol. 2007 February; 20(1):91; Comment in: J Interv Cardiol. 2006 December; 19(6):483-4; Percutaneous transcatheter repair for mitral regurgitation; Block P C) may again benefit from accurate imaging of the transseptal puncture and valvular intervention.

Other applications of image guided alteration of anatomic structures may include injecting or otherwise delivering an agent, such as cells and/or pharmacologic agents into a localized region. Accurate localization of stem cell delivery to damaged myocardium is another example of such an application. Yet another application of image guided alteration of anatomic structures is the delivery of energy, such as electrical energy for ablating tissue, such as radio-frequency (RF) energy. RF ablation can be used to control or prevent arrhythmias, and it can be used to facilitate puncturing or penetrating through tissue. Visualization prior to or during the application of RF energy can be helpful in ensuring that there is adequate contact between the tissue and the RF energy delivery device. Creation of artificial connections between separate fluid chambers involves the placement of prosthetic conduits, and may benefit from optimal forward-looking procedural guidance. Percutaneous construction of artificial coronary arterial-venous vascular conduits has been proposed as a substitute for traditional coronary bypass surgery for the treatment of ischemic heart disease (see Circulation. 2001 May; 103 (21):2539-43. Percutaneous in situ coronary venous arterialization: report of the first human catheter-based coronary artery bypass. Oesterle S N, Reifart N, Hauptmann E, Hayase M, Yeung A C).

SUMMARY OF THE KNOWN ART

The patent literature contains descriptions of several devices designed to enhance transseptal puncture. A catheter coupled to a non-imaging ultrasound transceiver to measure tissue thickness for detection of the fossa ovalis has been described (see Stewart et al. Transseptal access tissue thickness sensing dilator devices and methods for fabricating and using same. U.S. Pat. No. 6,755,790 issued Jun. 29, 2004), however this device is limited by an inability to image the needle tip and the fossa ovalis, which may encumber the procedure, and is unable to guide interventions beyond the inter-atrial septum. A magnetic resonance imaging transseptal needle antenna has been developed (Lardo Albert C et al. Magnetic resonance imaging transseptal needle antenna, US Patent Publication 20010056232 A1 published Dec. 27, 2001).

However magnetic resonance imaging is expensive, available in few medical centers, contraindicated in patients with implants and incompatible with ferro-magnetic medical devices. Another device has been developed which locates the fossa ovalis on the basis of unique electric injury patterns (Schwartz. Method and device for transseptal facilitation based on injury patterns (U.S. Pat. No. 6,994,094 issued Feb. 7, 2006).

Another device has been described which detects the fossa ovalis with the use of a detector capable of evaluating the frequency and intensity of the return signal (Lesh et al. Method for accessing the left atrium of the heart by locating the fossa ovalis (U.S. Pat. No. 6,650,923, issued Nov. 18, 2003). These devices are limited by employing non-imaging modalities. Cardiooptics (Boulder, Colo.) manufactures a catheter that emits infrared light and can image through flowing blood in real time. A device based on this technology is being developed to identify the fossa ovalis and enhance transseptal puncture. However this technology is not expected to visualize the advancement of the needle tip beyond the inter-atrial septum, and would therefore not be able to guide the degree of needle advancement into the left atrium so as to avoid puncture of the atrial free wall. Optically guided penetration catheters have been described (Patrick Macaulay et al. Optically guided penetration catheters and their methods of use, US Patent Publication No. 20060241342 published Oct. 26, 2006).

Sahn et al have presented results on a forward-looking ultrasound catheter that uses an array of ultrasound transducers combined with an ablation electrode to visualize cardiac structures and ablate myocardium. The device has a steerable tip that allows the user to take advantage of the image guidance and direct the ablation therapy to the desired site, (see J Am Coll Cardiol. 2007; Mar. 6, 2007, vol 49 (9):supplement 1. Experimental Studies With a 9-French Forward-Looking Intracardiac Imaging and Ablation Catheter Developed in a National Institutes of Health Supported Bioengineering Research Partnership Grant Program. ACC Abstract 846-3. David J. Sahn, Kalyanam Shivkumar, Aman Majahan, Muhammad Ashraf, Long Liu, Jonathan Cannata, Xunchang Chen, Raymond Chia, Aaron Dentinger, Matthew O'Donnell, K. Kirk Shung, Douglas N. Stephens, Kai Thomenius).

The publication to Degertkin et. al. (see IEEE Transactions on Ultrasonics, Ferroelectrics and Frequency Control. 2006; 53(2)2:474-82. Annular-ring CMUT arrays for forward-looking IVUS: transducer characterization and imaging. Degertekin F L, Guldiken R O, Karaman M) and Yeh et al (see IEEE Transactions on Ultrasonics, Ferroelectrics and Frequency Control. 2006; 53(6):1202-11. 3-D ultrasound imaging using a forward-looking CMUT ring array for intravascular/intracardiac applications. Yeh D T, Oralkan O, Wygant I O, O'Donnell M, Khuri-Yakub B T) describe a ring array of capacitive micromachined ultrasound transducers (CMUTs) through which a wire can be pushed through a lumen in the center of the ring array. The ring array provides forward-looking 3D imaging, but the imaging quality achieved to date with CMUTs is not adequate for most uses.

More recently, Courtney, Munce et al (U.S. patent application Ser. Nos. 12/010,208 and 12/010,206), incorporated herein by reference in their entirety) describe imaging probes that are able to produce forward looking, 3D images using novel mechanical scanning mechanisms (i.e. without the use of phased arrays) to enable acoustic and/or optical imaging. The present invention is adapted to include at least one such probe. The description of Courtney, Munce et al describes compact scanning mechanisms that enable volumetric imaging in either a forward-looking or side-viewing configuration.

Forward-looking configurations refer to configurations that allow imaging of a region located generally distal to the position of the scanning mechanism along the longitudinal axis of a probe. Side-viewing configurations refer to configurations that allow imaging of a region located generally lateral to the position of the scanning mechanism. The imaging probe generally comprises an ultrasound transducer and/or a fiber optic in combination with a variety of scanning mechanisms that direct light or acoustic energy over a desired volume to be imaged. Broadly, the scanning mechanisms described exploit forces such as, but not limited to, electrostatic forces, magnetic forces, elastic forces, centripetal forces and/or hydrofoil forces.

In certain embodiments, the extent of these forces (such as centripetal and/or hydrofoil forces) are altered by changes in the speed of rotation of the imaging probe around its longitudinal axis, which allows for an additional degree of freedom in the scanning mechanism.

Finally, several three-dimensional configurations of the transeptal catheter (Buck et al. Guiding sheath having three-dimensional distal end. U.S. Pat. No. 6,004,280. Dec. 21, 1999 AND Gurusamy Ravisankar et al. Transseptal puncture needles and needle assemblies. US Publication 2006-0064062-A1. Mar. 23, 2006) and mechanisms for deflecting the distal end of a catheter (Badger et al., see U.S. Pat. Nos. 4,898,577 and 5,030,204) are known in the prior art.

SUMMARY OF THE INVENTION

Catheter-based devices are provided to facilitate image guided manipulation and/or sensing of anatomic structures. Specifically, the devices are adapted to incorporate the use of an imaging probe.

The present invention provides a catheter system, comprising:

an elongate catheter having proximal and distal ends, the elongate catheter being insertable, distal end first, into a natural or human-made lumen within the body of a mammalian patient;

a medical device with its functional component near said distal end of said elongate catheter that is advanceable to a target location in the vicinity of the distal end of the catheter; and a forward-looking imaging probe incorporated into a rotatable shaft in said distal end of said elongate catheter, said imaging probe including transducers for one, or both of, optical coherence tomography imaging and ultrasound imaging, said imaging probe configured to scan a field of view for determining a position of the target location within the patient's body relative to indicia of a trajectory on which the medical device will advance such that the operator may adjust the position and/or rotational orientation of the catheter within the lumen such that when the medical device is subsequently advanced, the medical device will enter the target location in the field of view.

The imaging probe may include a means for estimating a rotational motion near the distal end of the rotating shaft within the probe.

In a particular embodiment of the present invention, a transseptal puncture catheter is adapted to include a forward-looking ultrasound-imaging probe near the tip of the puncture catheter. This embodiment integrates the imaging and interventional components, and enable real-time simultaneous visualization of the needle tip, fossa ovalis and left atrial cavity. The device will facilitate safe and accurate puncture of the inter-atrial septum, positioning of the needle within the left atrium and access to the anatomical targets of the procedure.

The integration of a forward-looking imaging system with a puncture catheter system can be readily adapted to be applied to other body chambers and/or lumens. For example, it could be adapted for use in the creation of arteriovenous fistulas for dialysis access, percutaneous venous bypass grafts and transhepatic intraportal shunt (TIPS) procedures.

In another embodiment, a catheter-based system adapted to include an imaging probe can be further adapted to incorporate an injection mechanism. Such a system could be used to enable image-guided injections, such as stem cell injections into tissues such as the heart wall, chemotherapeutic agents into a malignant mass or antibiotics into an abscess, where precise localization of the region of delivery may be required. Alternatively, a needle can be used to aspirate fluid or soft tissue under image guidance.

In yet another embodiment, a catheter-based system adapted to include an imaging probe can be further adapted to include one or more electrodes. The one or more electrodes can be used to facilitate electrophysiological measurements and/or ablation via connection to an electrical energy source such as an RF energy source.

The present invention also provides a method for penetrating a target within the body of a mammalian patient, comprising the steps of:

(a) providing a catheter system, comprising:

an elongate catheter having proximal and distal ends, the elongate catheter being insertable, distal end first, into a natural or human-made lumen within the body of a mammalian patient;

a medical device with its functional component near said distal end of said elongate catheter that is advanceable to a target location in the vicinity of the distal end of the catheter; and a forward looking imaging probe incorporated into a rotatable shaft in said distal end of said elongate catheter, said imaging probe including transducers for one, or both of, optical coherence tomography imaging and ultrasound imaging, said imaging probe configured to scan a field of view for determining a position of the target location within the patient's body relative to indicia of a trajectory on which the medical device will advance such that the operator may adjust the position and/or rotational orientation of the catheter within the lumen such that when the medical device is subsequently advanced, the medical device will enter the target location in the field of view;

(b) inserting the catheter into the natural or human-made lumen within the body of the mammalian patient;

(c) obtaining an image consisting of the field of view of the imaging probe and determining, using said image, the position of the target location within the patient's body relative to indicia of a trajectory on which the medical device will advance;

(d) adjusting, if necessary, the position and/or rotational orientation of the catheter system within the natural or human-made lumen such that the catheter is in a position and rotational orientation wherein when the medical device is advanced, the medical device will enter the target location in the field of view of the imaging probe; and (e) advancing the medical device from the catheter to the target location.

A further understanding of the functional and advantageous aspects of the invention can be realized by reference to the following detailed description and drawings.

BRIEF DESCRIPTION OF THE DRAWING

Preferred embodiments of the invention will now be described, by way of example only, with reference to the drawings, in which:

FIG. 4A is a diagram of the present invention that combines a transeptal puncture mechanism with an image guidance mechanism that images a volume near the distal end of the puncture catheter assembly;

FIG. 4B is an enlarged diagram of the distal end of the catheter assembly. FIG. 4C is a cross-sectional diagram along the length of the main body of the catheter assembly;

FIG. 9 shows the catheter outfitted with an electrical conductor;

FIG. 10 shows the catheter outfitted with a biopsy forceps;

FIG. 12 shows the catheter outfitted with a penetration needle through which a guide-wire is inserted.

DETAILED DESCRIPTION OF THE INVENTION

Without limitation, the majority of the systems described herein are directed to an imaging probe using either optical or ultrasonic (or both) imaging. The imaging probe may include means for estimating a rotational motion near the distal end of a rotating shaft within the probe. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an imaging probe.

As used herein, the term "about", when used in conjunction with ranges of dimensions, temperatures or other physical properties or characteristics is meant to cover slight variations that may exist in the upper and lower limits of the ranges of dimensions as to not exclude embodiments where on average most of the dimensions are satisfied but where statistically dimensions may exist outside this region. For example, in embodiments of the present invention dimensions of components of an imaging probe are given but it will be understood that these are not meant to be limiting.

Figure 1:
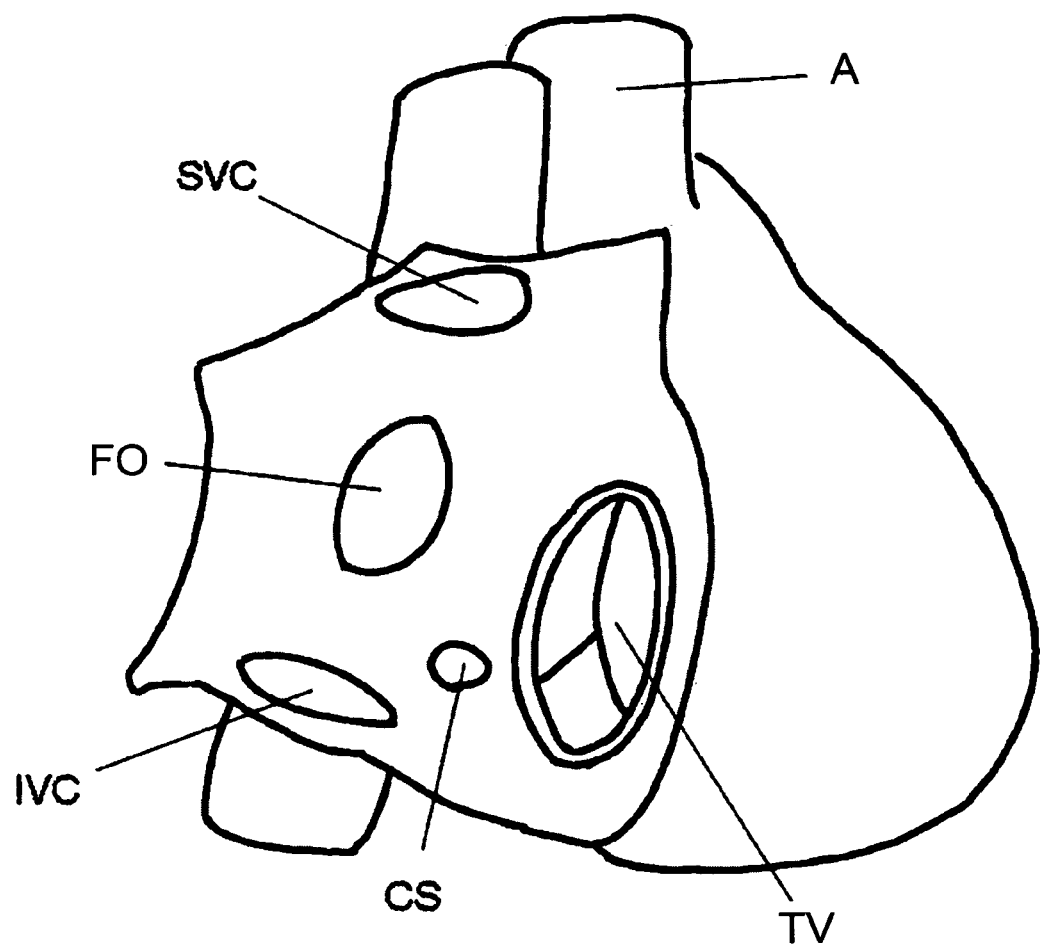
FIG. 1 is an illustration of the inner chamber of the right atrium, facing towards the fossa ovalis.

FIG. 1 shows a diagrammatic representation of the anatomy of some relevant cardiac structures. A line diagram of the right atrium of the heart is shown, with its outer wall cut open so that relevant structures within the right atrium (RA) can be seen. The right atrium receives blood from the inferior vena cava (IVC) and superior vena cava (SVC). It also receives blood from the coronary circulation via the coronary sinus (CS). Blood from the right atrium empties into the right ventricle via the tricuspid valve (TV). The fossa ovalis (FO), part of the septum that lies between the right and left atria, is demonstrated with its approximate position relative to the other structures. A medical practitioner often wishes to puncture through the fossa ovalis to get access to the left atrium, which lies on the other side of the fossa. A denotes aorta.

Figure 2A:
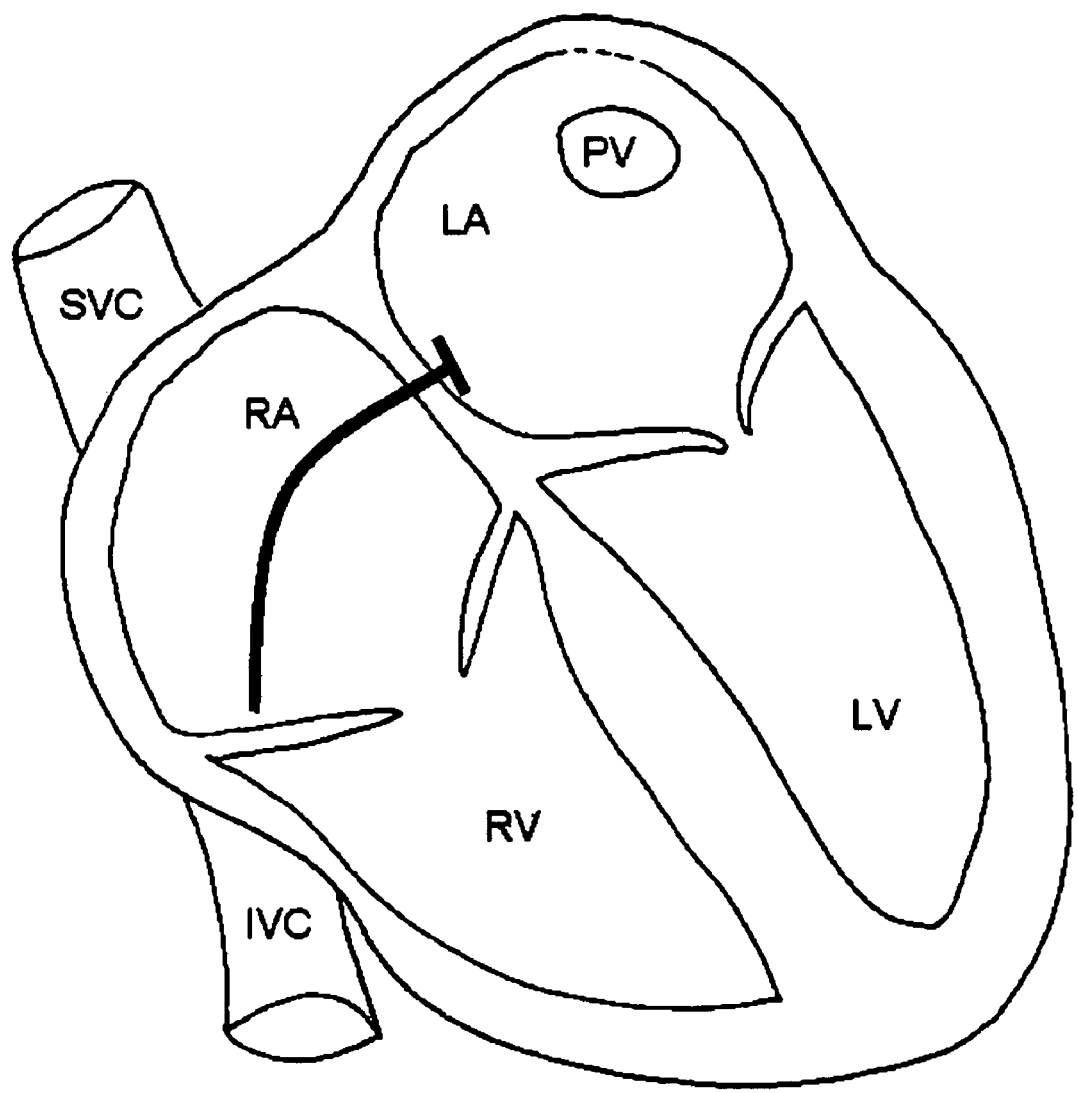
FIG. 2A through 2E illustrate the four (4) chambers of the heart, demonstrating examples of therapeutic procedures towards which the present invention can be applied.

FIGS. 2A through 2E show a longitudinal four-chamber cutaway or cross section of the heart to illustrate some of the locations to which a medical practitioner may wish to access once having accomplished transseptal puncture. An occluding device, such as an Amplatzer Septal Occluder, may be delivered across the atrial septum to close an atrial septal defect, or a patent foramen ovale. FIG. 2A shows the approximate pathway and final position for which such a device would be placed in relation to the right atrium (RA) and left atrium (LA).

Figure 2B:
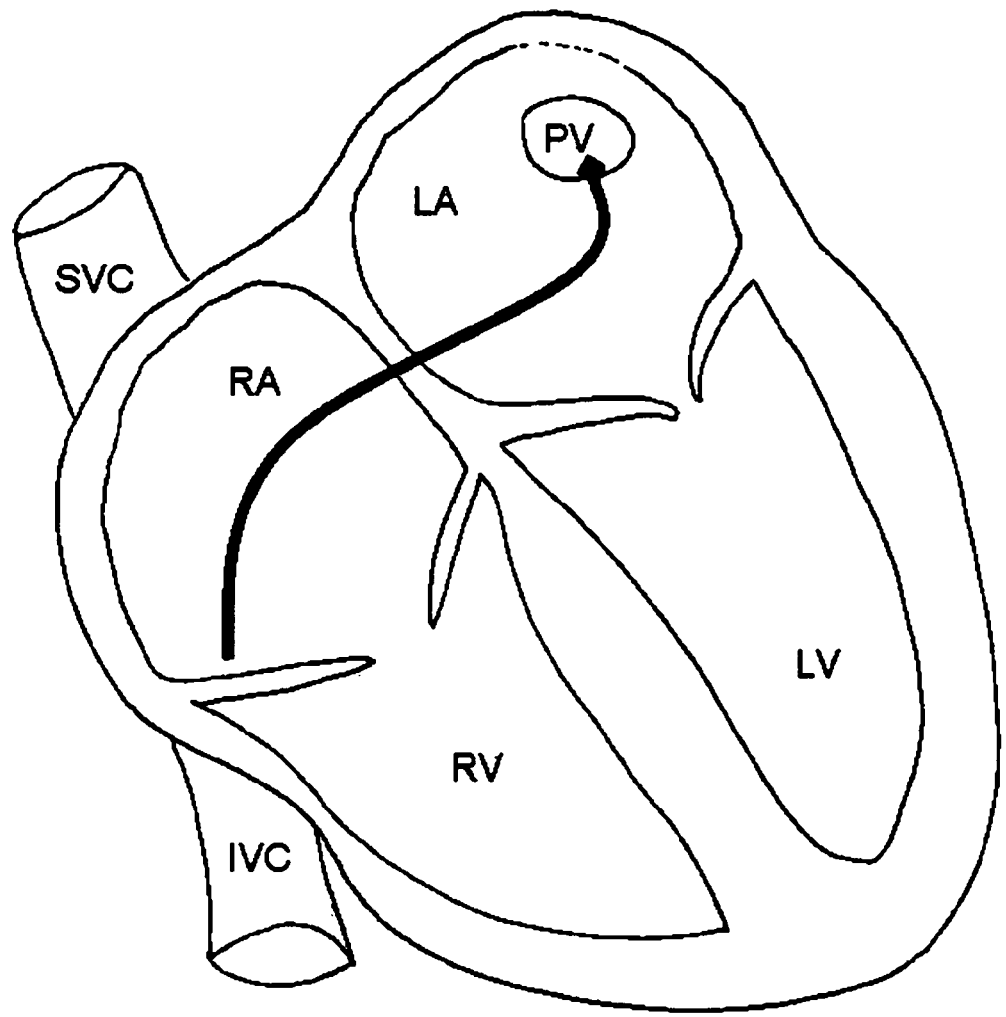
Figure 2C:
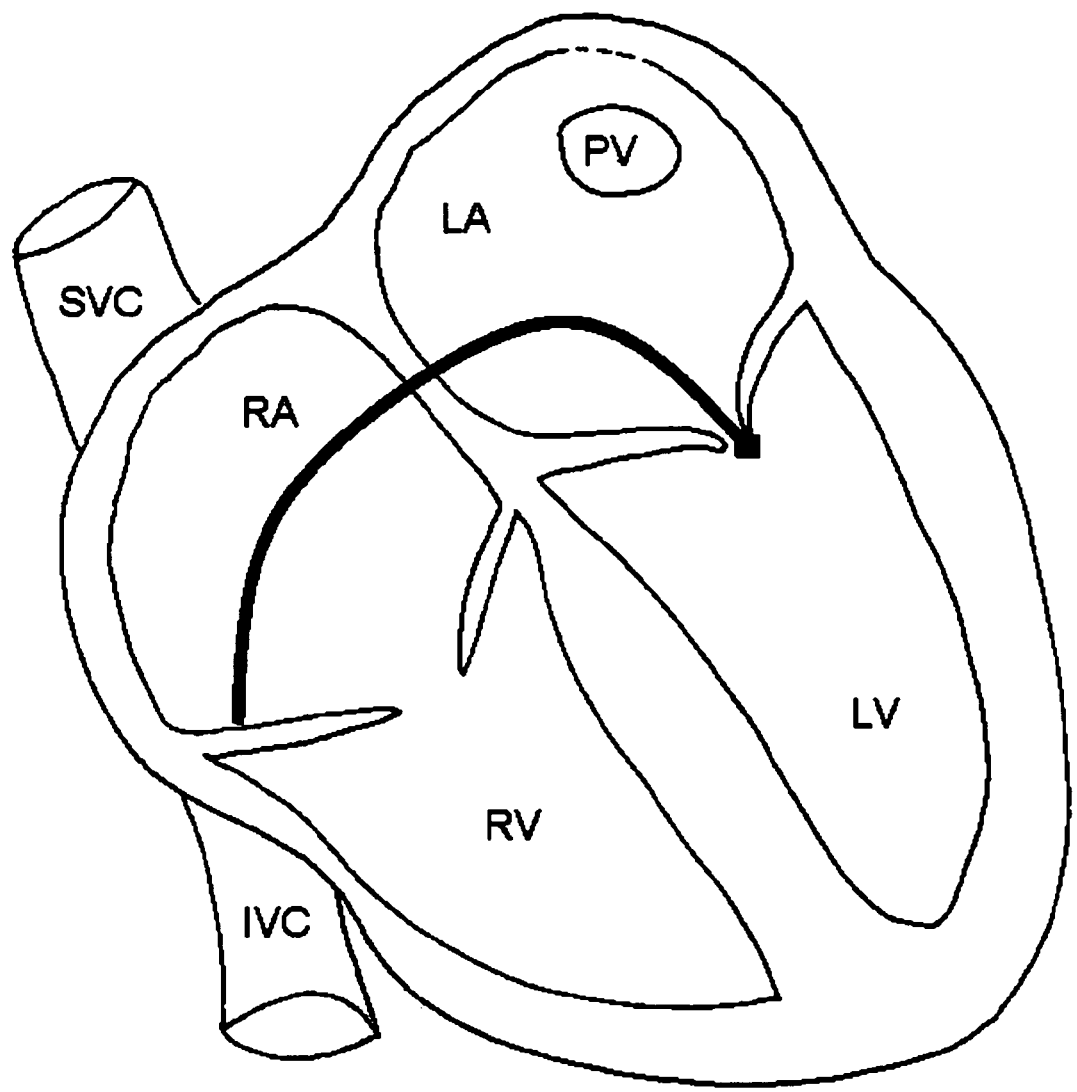
Figure 2D:
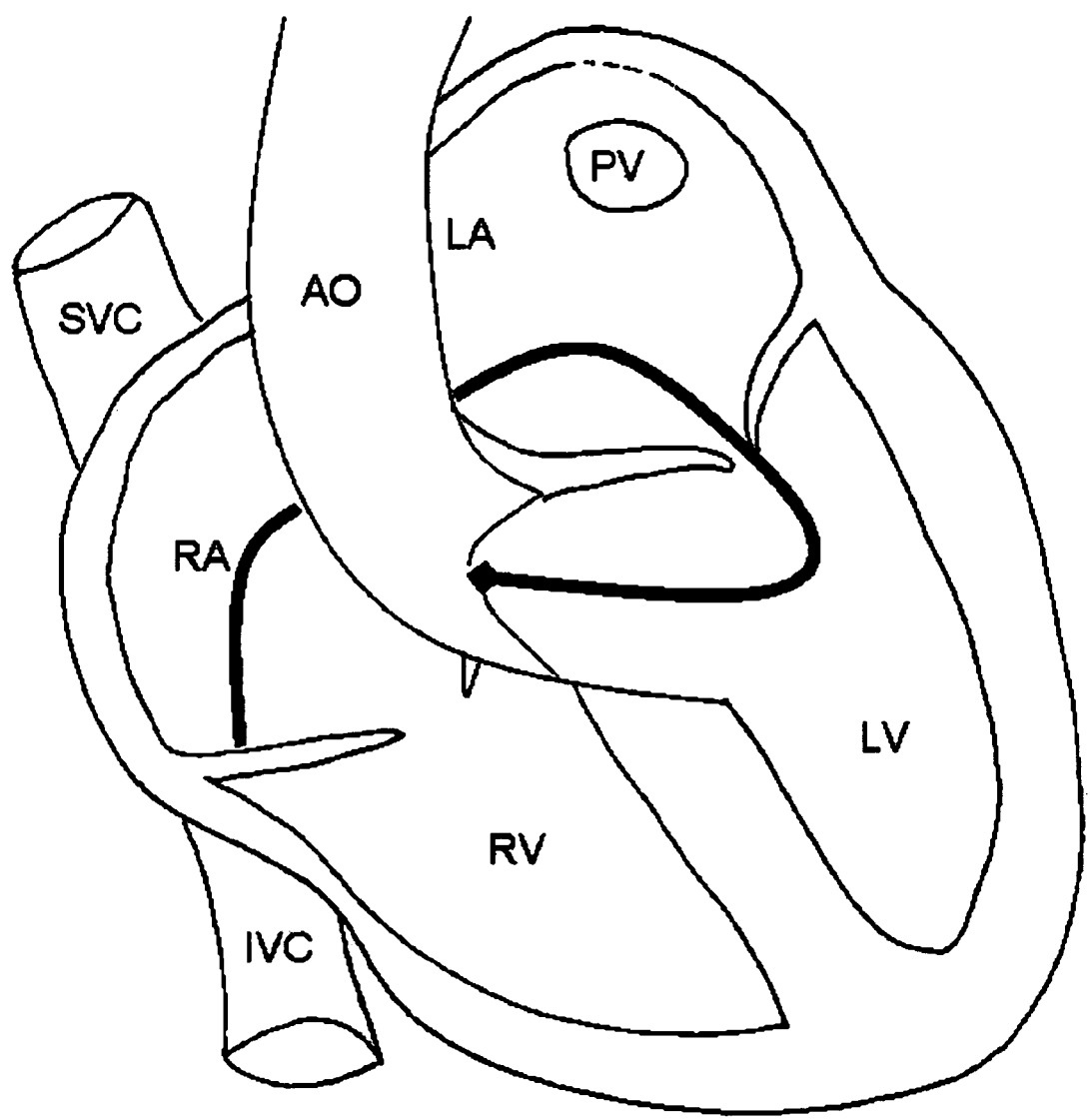
Figure 2E:
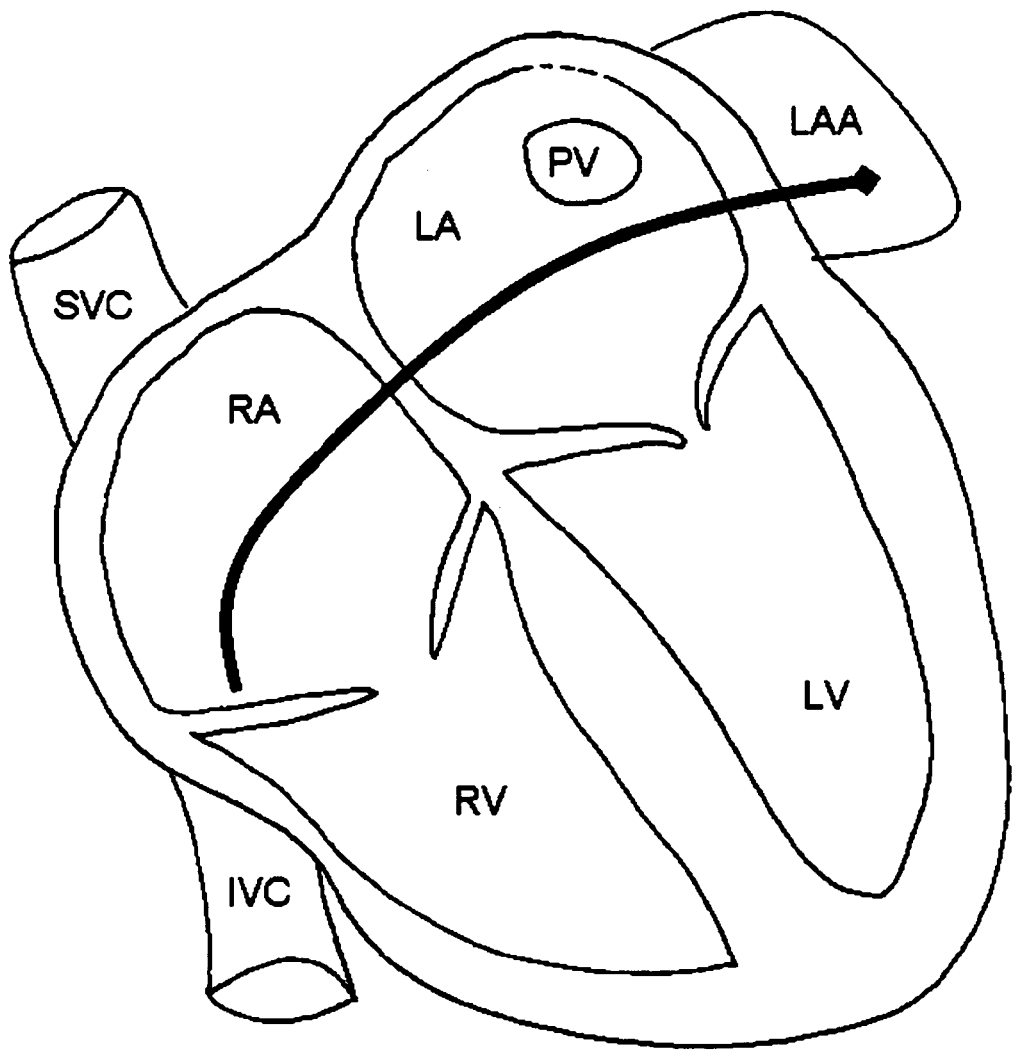

FIG. 2B shows the approximate pathway and final position for which one might access the pulmonary veins (PV) in the left atrium via a transseptal access point from the right atrium. Pulmonary vein ablation is an increasingly common procedure for treatment of atrial fibrillation. FIG. 2C shows the approximate pathway and final position for which one might access the area adjacent to the mitral annulus and mitral valve via a transseptal access point from the right atrium. FIG. 2D shows the approximate pathway and final position for which one might access the area adjacent to the aortic valve via a transseptal access point from the right atrium. FIG. 2E shows the approximate pathway and final position for which one might access the area adjacent to the left atrial appendage via a transseptal access point from the right atrium.

Figure 3A:
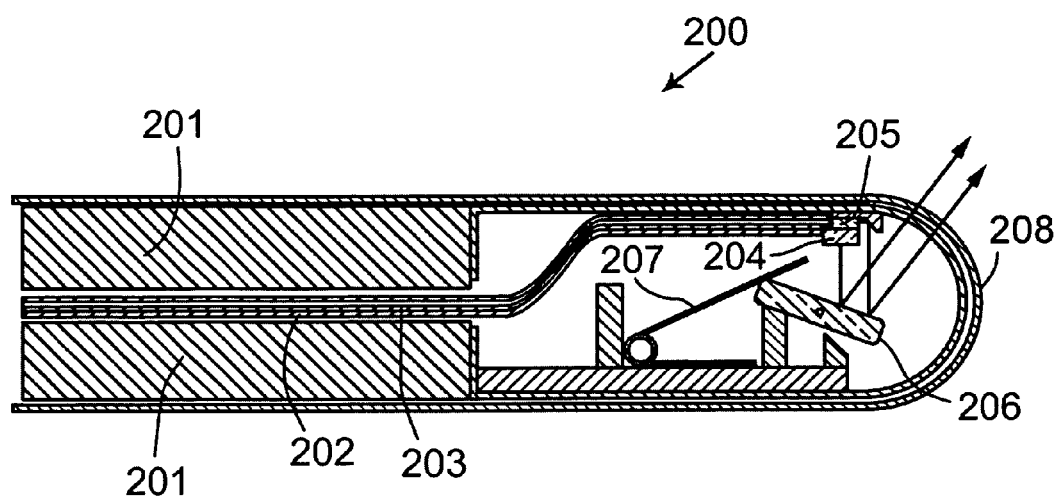
FIGS. 3A through 3D depict an example of an imaging system capable of forward viewing imaging for which the present invention is adapted to incorporate.

FIG. 3A shows a representative embodiment of a forward-looking imaging system as disclosed in U.S. patent application Ser. Nos. 12/010,208 and 12/010,206 both filed Jan. 22, 2008 to Courtney et al. and both being incorporated herein by reference in their entirety. A summary of a representative embodiment of the invention by Courtney et al is provided to illustrate how the current invention is adapated in order to use the images produced to facilitate specific procedures, although many of the embodiments of the invention described by Courtney et al can be substituted for the illustrated example in the present description.

Figure 3B:
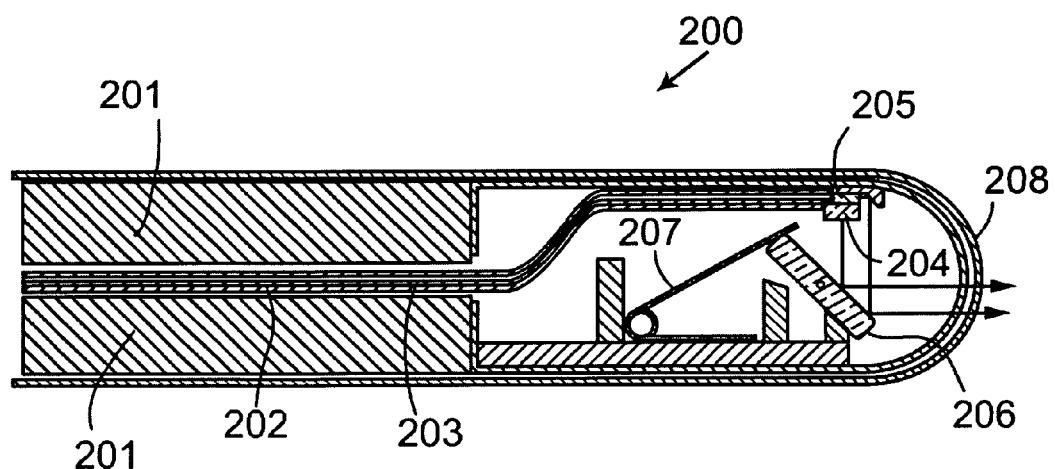

The imaging probe 200 shown in FIGS. 3A and 3B comprises an imaging shaft 201 containing either one or more electrical conductors 202, one or more fiber optic waveguides 203 or both. An ultrasound transducer 204 or a lens and reflective assembly 205 transmit imaging energy either directly towards tissue (not shown) or indirectly towards tissue via a deflecting mechanism 206 such as a mirror. The ultrasound energy and/or the optical energy are directed towards tissue and can be back reflected from interfaces in the tissue towards the ultrasound transducer or the lens and fiber optic assembly. This energy is detected and used to create ultrasound images and/or images based on optical imaging such as optical coherence tomography images.

The imaging shaft rotates around its longitudinal axis. In the example imaging probe depicted in FIGS. 3A and 3B, when the shaft 201 is rotating at a constant speed, the imaging energy is directed out of the catheter at a given angle. As the rotational velocity is adjusted, the imaging angle is changed. A restoring force, such as that provided by a spring 207, causes the imaging angle to have a preferred angle at slow rotational speeds. However, as the rotational speed is increased, the imaging angle will change.

The imaging probe 200 is encased within the lumen of an external sheath 208. Materials for the external sheath may include but is not limited to one or more polymers, such as pebax, nylon, polyethylene, PEEK (polyetheretherketone), PTFE (Teflon), or other materials known in the art of catheter manufacture.

Figure 3C:
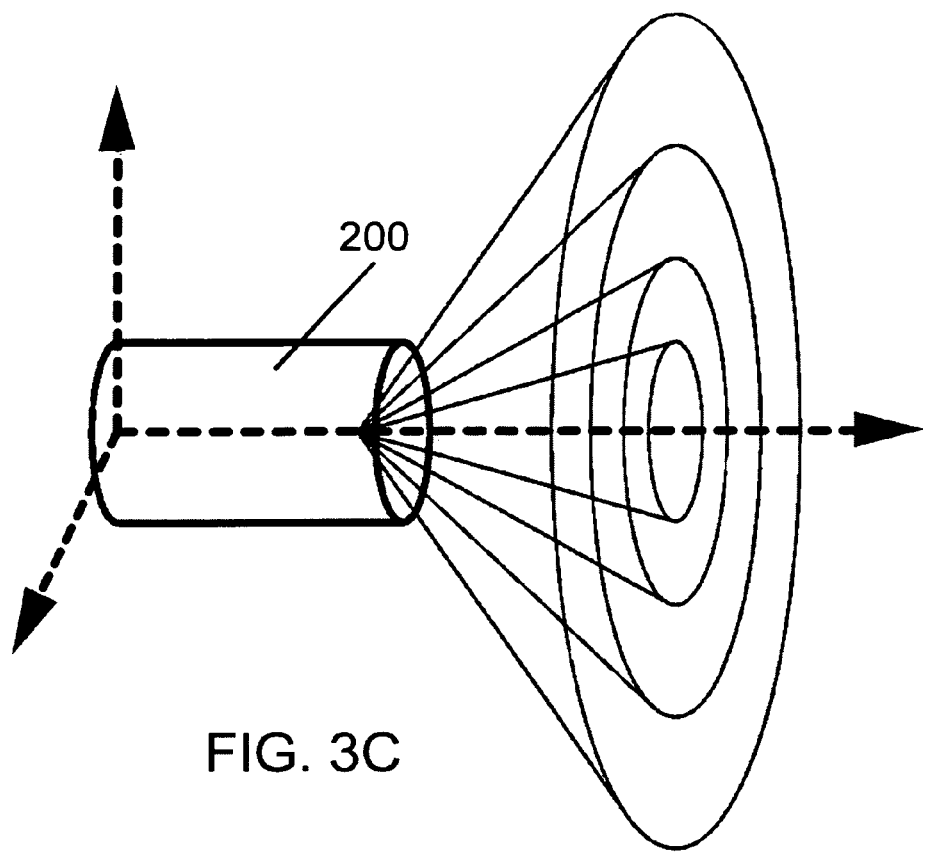
Figure 3D:
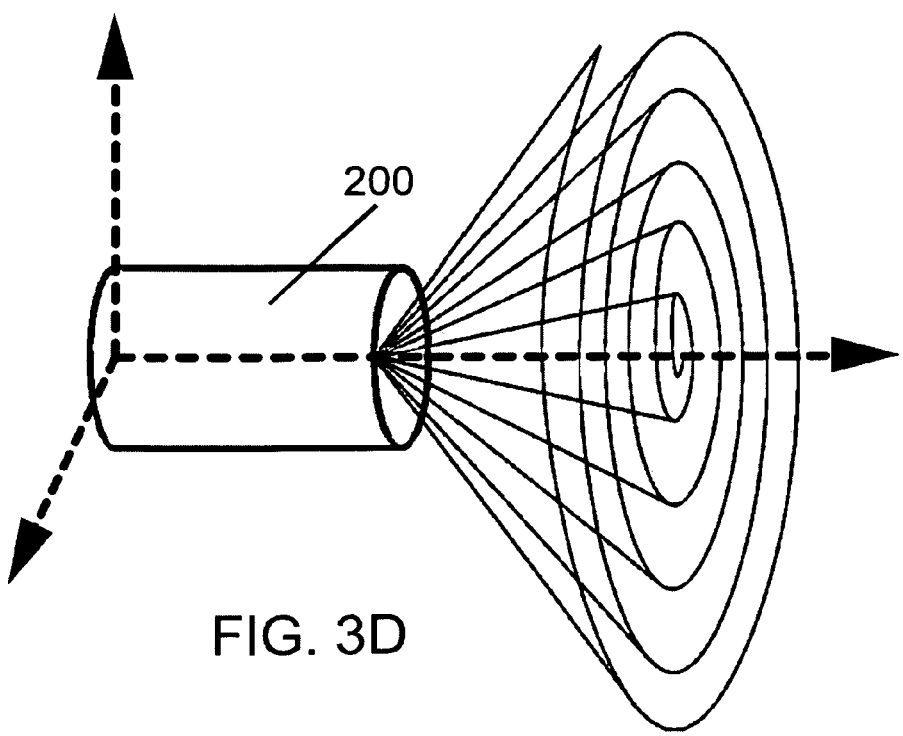

In FIG. 3B, the deflector is seen to have changed its orientation as a result of centripetal acceleration. Therefore, a 3D imaging dataset in a forward-looking direction can be collected using either acoustic or optical imaging energy by varying the rotational speed. FIG. 3C shows the scanning pattern that would occur if imaging data was collected using a series of discrete rotational speeds, with a separate cone imaged for each rotational speed. FIG. 3D shows the scanning pattern that would occur if the imaging data was collected by having the imaging shaft rotate through a continuous range of rotational speeds, thus causing the path of the imaging energy beam to follow a spiral trajectory.

FIG. 4A shows a catheter assembly configured for penetrating across a septum under image guidance. An outer sheath 101 extends from a proximal hub 113 to a distal end. A dilator 102 comprises an elongate shaft that fits with the inner lumen of the outer sheath 101. The distal end of the dilator 102 has a tapered tip 114 that is designed to stretch the tissue of the atrial septum by making a larger hole as it is advanced through the septum. FIG. 4B shows more details of distal tapered tip 114. It may have a coating such as a Teflon coating or other coating, such as a hydrophilic coating to help ease passage through the tissue. Referring to FIG. 4C, the dilator 102 has an inner needle-carrying lumen 111 that is adapted to allow passage of a needle 104 from the proximal end of the dilator to the distal tip. The needle 104 may be hollow (as shown in FIG. 4C) or solid. If the needle is 104 hollow, it will have a further inner lumen adapted to receive a guide wire or stylet 105.

Advancement of a sharp needle tip through the needle-carrying lumen 111 of a bendable device such as a polymer catheter can on occasion allow the needle tip to puncture through the body of the catheter and thus damage the mechanical integrity of the catheter system. For this reason, it may be desirable to construct the inner surface of all or a portion of the needle-carrying lumen 111 with one or more materials that are resistant to needle puncture. For example, a portion, such as the distal portion, or the entire length of the needle carrying lumen 111 can be lined with a hypotube, such as stainless steel hypotube. In such a configuration, the needle carrying lumen would be protected from the sharp needle tip by the hypotube as the needle is advanced. Alternatively, the needle can be advanced with a surrounding hypotube to protect the catheter body, whereby the hypotube is not an integral part of the catheter body.

Referring to FIGS. 4A, 4B and 4C, during the procedure, a significant portion of the assembly from the proximal hub 113

(FIG. 4A) to the distal tip 114 will be located inside the patient's cardiovascular system, with a point of entry from a vein, preferably from a femoral vein, but potentially from an alternative site such as an internal jugular vein or a subclavian vein. The dilator 102, outer sheath 101 and/or needle 104 may have a preformed curvature 115 (FIG. 4A) near their distal end that biases the entire assembly to be able to curve from its entry point into the right atrium towards the fossa ovalis, which is on the left posterior wall of the right atrium. The preformed curvature 115 may be induced by several methods known in the art of catheter manufacturing, such as thermoforming, curing, adding one or more external heat shrink layers or incorporation of shaped memory elements, such as nitinol or stainless steel braiding. The dilator 102 may have an optional indicator arm 112 (FIG. 4A) that extends from the main shaft of the dilator 102 in a direction such that the indicator arm 112 provides an external feature that can referred to by the user of the device to indicate the general direction in which the preformed curvature 115 lies. The curvature shown in FIG. 4A is a simple arc, but can assume a more complex curvature to better adapt to the anatomy into which the device is delivered.

The shaft 103 of an imaging probe also extends through the dilator 102 via an imaging probe lumen 116. The imaging shaft 103 extends along a substantial portion of the length of the dilator 102 and may be able to rotate within the imaging probe lumen 116 as part of its scanning mechanism for generating images.

FIG. 4B provides a magnified view of the distal tip of the catheter assembly, including the external sheath 101 and the distal tip 114 of the dilator 102 that can extend beyond the distal end of the external sheath 101. The needle 104 and the optional wire 105 are seen to be capable of extending beyond the distal tip of the dilator. Preferably, the wire 105 is longer than the needle 104, which is longer than the dilator 102, which is long than the outer sheath 101, and each of these components can translate coaxially in an independent manner.

The distal tip of the dilator 114 also contains an imaging window 106 that allows imaging energy, such as ultrasound, to escape from the inner confines of the dilator towards a volume of interest near the distal tip of the catheter assembly. The imaging window may surround the entire circumference of the dilator, or just a portion of the circumference as depicted in FIG. 4B. The imaging window may also extend completely to the distal end of the dilator tip or stop more proximally, as depicted in FIG. 4B. Preferably, the field of view for imaging can include the volume of interest in which the distal ends of the needle 104 and/or wire 105 reside during the process of puncturing the septum. This allows the user to receive image guidance for the procedure by means of the imaging console 108 to which an imaging assembly is connected. Preferably, the imaging energy is ultrasound, but may alternatively include optical imaging methods, such as angioscopy, infra-red imaging and/or optical coherence tomography. The advantage of ultrasound over the optical methods is generally better penetration through a blood-filled field.

The distal tip of the dilator 102 may have a concentric taper, whereby it tapers evenly around its entire circumference. Alternatively, it may have an eccentric taper, whereby there is a bias in the degree of the taper towards one particular side, such as having a more dramatic taper on the same general side of the dilator tip as the imaging window 106. The needle-carrying lumen 111 and/or the needle 104 (FIG. 4C) may optionally have a slight curvature near their distal ends that causes the needle 104 to exit the tip of the dilator 102 in a manner that direct the needle tip to be better centered within in the field of view. This adaptation would allow the needle tip to be more easily imaged during use of the device.

The imaging window 106 (FIG. 4B) located in the distal tip 114 of the dilator 102 is made of a material that is generally transparent to the imaging energy, but hard enough to withstand the normal forces that will be experienced while the dilator is pushed through the septal tissue. For acoustic imaging, the material may be any of several known to allow transmission of acoustic energy, including TPX, Pebax, Perspex, polycarbonate, acrylic and several others. The window 106 may be coated with a coating to minimize friction or improve biocompatibility. If the imaging modality is optical in nature, the window material can be selected as a material that has a low attenuation in the range of wavelengths of interest.

FIG. 4C shows the magnified cross-sectional image of the main portion of the catheter assembly. The outer sheath 101 is large enough to accept the dilator 102 that has both a needle-carrying lumen 111 and an imaging probe lumen 116. The needle carrying lumen 111 contains the needle 104. If the needle 104 is optionally hollow, it can be adapted to receive a guidewire 105 through the needle's inner lumen. The imaging probe lumen 116 is large enough to accept an imaging probe (such as probe 200 shown in FIGS. 3A and 3B), including the imaging probe shaft 103 shown in FIG. 4C but equivalent to imaging probe shaft 201 in FIGS. 3A and 3B.

The imaging probe shaft 103 is connected at its proximal end to an image-scanning controller 107 (FIG. 4A) which may include a motor drive unit. In the case where a motor drive unit is included as a component of the image-scanning controller 107, the imaging probe shaft 103 may be rotating within the imaging probe lumen 116 (FIG. 4C). Preferably, an additional imaging probe sheath (not shown), would extend from the image scanning controller 107 to a point near where the imaging probe enters the imaging probe lumen 116 to isolate it from the external environment.

There are several advantages derived from integrating the imaging platform and tissue puncturing mechanism into the same catheter, including easier control of the device, simpler alignment of the puncturing mechanism within the imaging device's field of view and the requirement for only a single peripheral vascular puncture to deliver the imaging functionality and the puncturing device to the desired region. Also, the wall of the imaging probe lumen 116 can obviate the need for an external sheath 208 that surrounds the imaging assembly and imaging probe shaft 103 when such an imaging probe is used on its own, such as without being integrated into the devices of the present invention as shown in FIGS. 3A and 3B. These advantages can lead to secondary advantages, including increased safety, faster overall procedure times and less time required for training physicians to perform the desired procedure. By obviating the need for a separate external sheath 208 (FIGS. 3A and 3B) for the imaging probe, the present invention allows for a more compact design. It also allows for improved transmission of imaging energy as the external sheath would add another layer of material through which the imaging energy must travel, whereby such layers reduce the intensity of the imaging energy, such as by attenuation or by reflections at the interfaces of the layers.

Figure 5A:
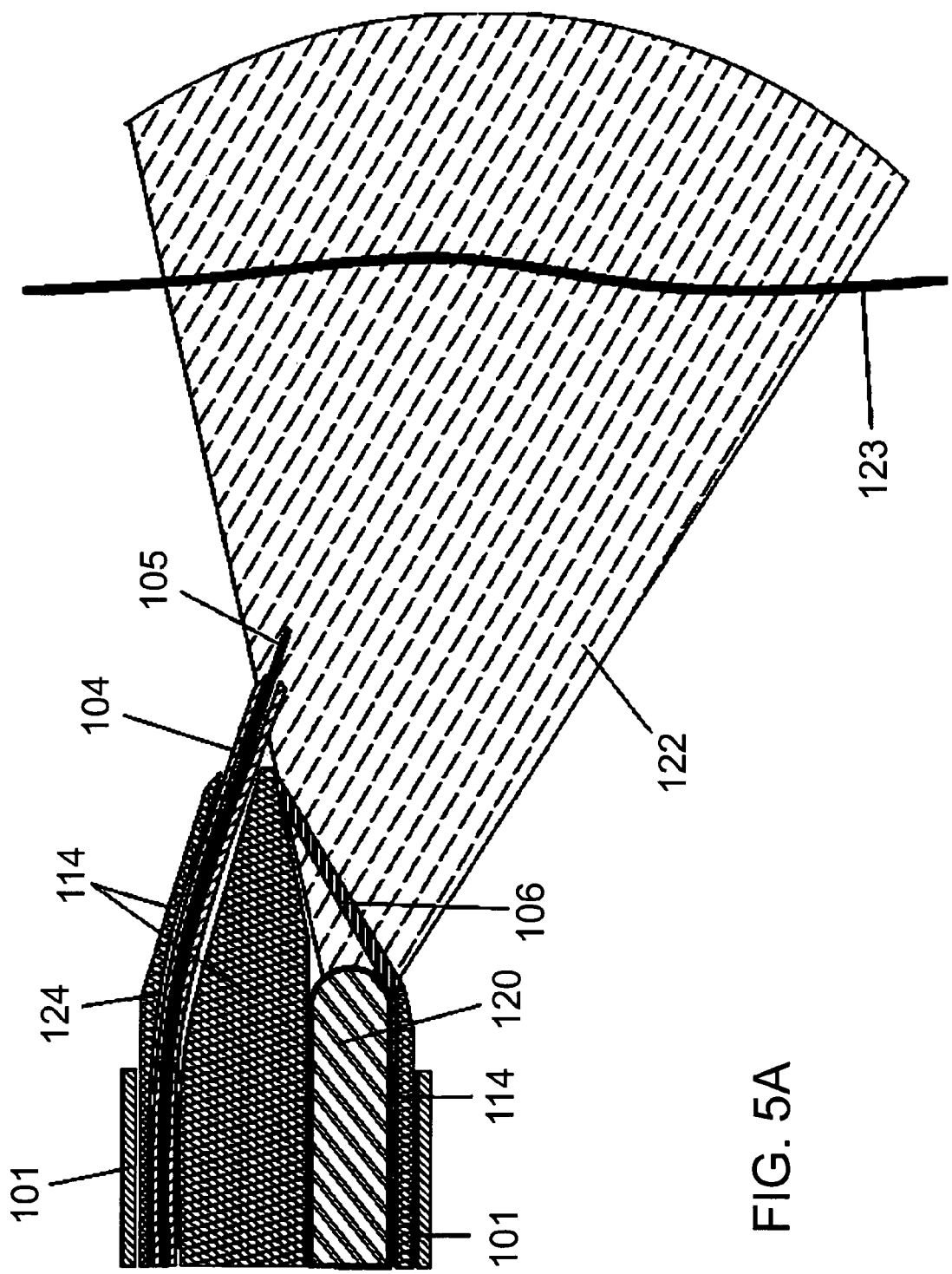
FIGS. 5A and 5B show a longitudinal cross-sectional schematic diagrams of two representative embodiments of the tip of a puncturing mechanism that incorporates image guidance.

FIG. 5A shows a longitudinal cross-section of the distal portion 114 of the catheter assembly. The distal end 114 of the dilator 102 has a channel 124 adapted to receive the needle 104 and the stylet 105. The channel 124 may optionally have a curvature in it to direct the needle 104 into the field of view 122 of imaging assembly 120. The imaging assembly 120 can be any of the imaging assemblies capable of forward-viewing, such as imaging probe 200 shown in FIGS. 3A and 3B, as described by Courtney et al. (U.S. patent application Ser. Nos. 12/010,208 and 12/010,206), incorporated herein by reference in their entirety. By having the tip of needle 104 included with the field of view 122, an operator can visualize the procedure of having the needle 104 advance and puncture through an anatomic structure such as a septum 123. Adjacent to the distal end of the imaging assembly 120 is the imaging window 106.

Figure 5B:
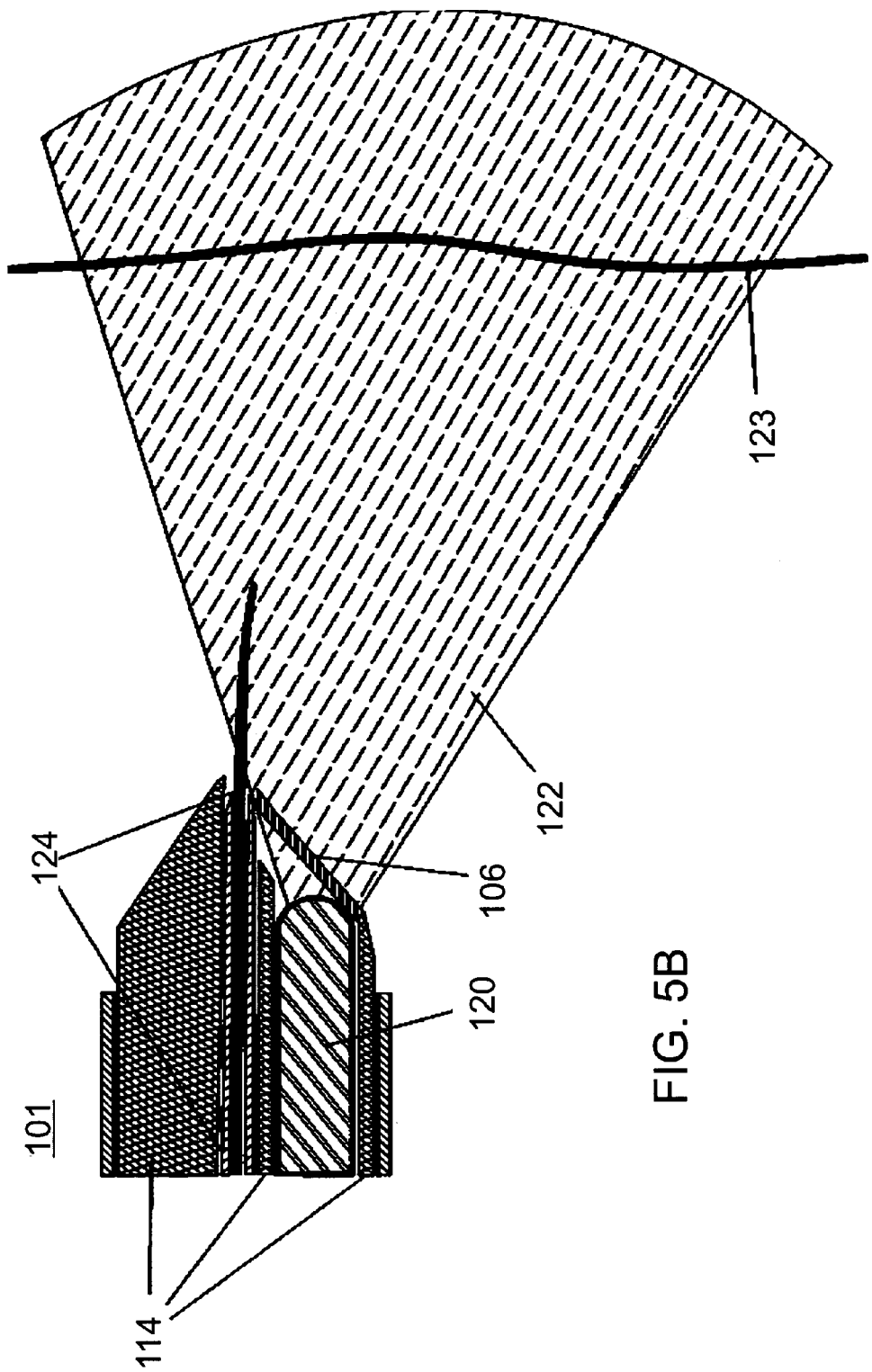

FIG. 5B shows a slightly different embodiment where the needle channel 124 is more closely aligned to the center of the dilator 102. The needle-tip in this case will have less of a bias towards reaching the center of the field of view 122 of the imaging assembly, but is simpler to construct and may have advantages with respect to simplicity for the user in coordinating the needle's action during puncturing with the images generated by the imaging assembly 120.

Figure 6B:
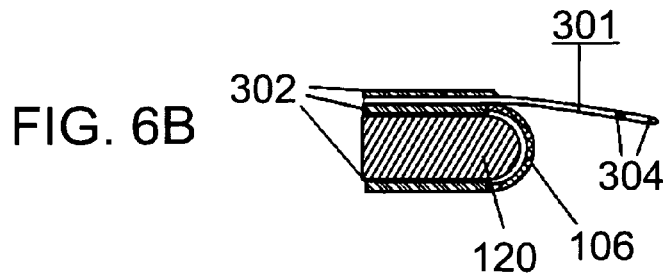
FIGS. 6A and 6B show a catheter assembly for delivering electrical energy, such as radiofrequency energy, under image guidance.
Figure 6A:
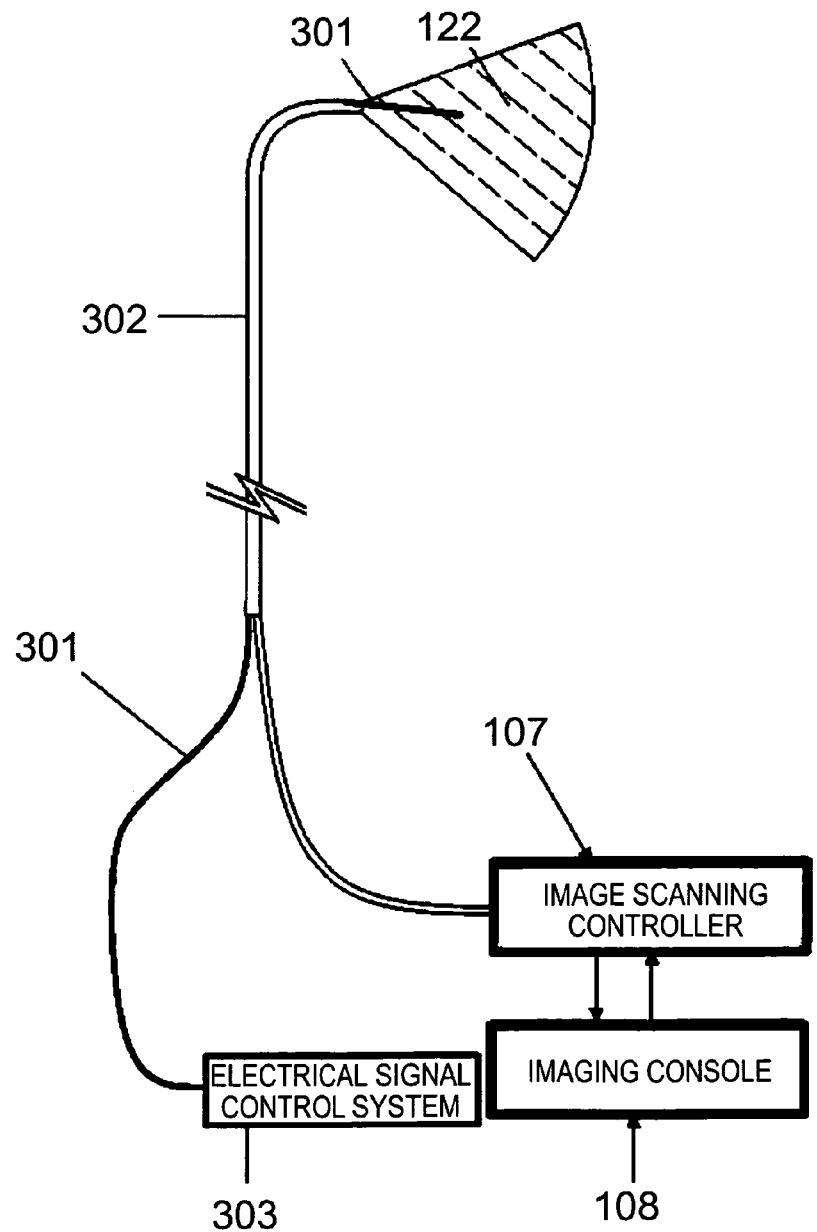

FIG. 6A shows an imaging probe adapted for use in combination with an integrated series of electrical conductors 301, for either sensing and/or delivery of electrical energy to tissue visualized by the imaging probe. One or more series of electrical conductors 301 can travel along the length of the catheter 302. The distal end of at least one of the electrical conductors 301 will be in the field of view 122 of the imaging assembly 120. Each conductor 301 is designed to be in contact with the body or a body fluid via a surface electrode 304 near the distal end of each conductor. An electrical signal control system 303 is connected to the conductors to route the electrical signals and either measure the signals sensed or deliver the required electrical energy to the conductors for therapeutic means.

Measurement of electrical activity of the cardiac and/or nervous system is commonplace in modern medicine. It is also common to deliver electrical energy, such as radiofrequency ("RF") energy to these tissues for therapeutic purposes. Such electrical energy can be used to ablate tissue, thus reducing its potential to create unfavourable arrhythmias. Alternatively, the ablation can create a channel or puncture a hole through the tissue. Indeed, the ablation functionality depicted in FIG. 6A could be combined with the mechanical device for puncturing through a septum as seen in FIG. 4A.

FIG. 6B provides a closer view of the distal end of the catheter 302 in a longitudinal cross-sectional view. A channel for incorporating one or more of the integrated electrical conductors 301 is provided that connects to surface electrodes 304. An electrical insulator may cover the conductors 301 either within the channel and/or once they exit the catheter body 302. The imaging assembly 120 is incorporated within the catheter and an imaging window 106 is provided so that the imaging assembly 120 can visualize structures through the imaging window 106.

The ability to visualize the structures to which the energy is delivered or from which electrical activity is measured will foreseeably help with increasing the accuracy of these procedures and reducing the time required to position the electrodes 304 in the desired region. Again, the integration of the imaging device with a therapeutic or electrodiagnostic device requires only a single vascular puncture and has the potential to simplify procedures requiring either sensing or delivery of electrical energy to a desired anatomical location. Image guidance can also help ensure that there is adequate contact of the ablative means with the target tissue at the time of attempted ablation.

It will be understood that while the figures show a needle or electrode attached to the distal end of the catheter system, it will be appreciated that any medical device could be attached thereto depending on the intended application and use of the catheter system. For example, the medical device could be an interventional-medical device including, but not limited to a needle: or a tissue penetrator. Other interventional medical devices that could be used as part of the catheter system include biopsy forceps, valvuloplasty balloon, prosthetic valve, paravalvular leak occlusion device, septal or left atrial appendage closure device, injection needle, laser or radiofrequency energy source and percutaneous left ventricular assist device, to mention a few.

Additionally, catheters may be outfitted with transponders, transmitters, or receivers to help assess positioning and orientation of devices with the body. These may consist of one or more magnets or antennae. The Carto system (sold by Biosense Webster, a division of Johnson and Johnson) is an example of a system that relies on coils near the tip of a catheter while an external magnetic field is applied. The electrical signals from the coils are then used to identify the position and orientation of the catheter tip. Alternatively, a magnetopositioning system can be incorporated (see U.S. Pat. No. 7,386,339). Alternatively, the transmitters/receivers can be used to wirelessly transmit information from the catheter tip.

Figure 7B:
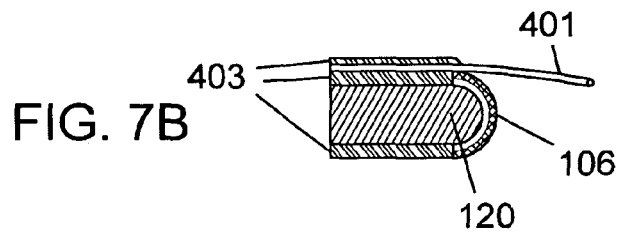
FIGS. 7A and 7B show a catheter assembly for locally injecting a user-selected medium, such as cells or pharmaceutical agents, under image guidance.
Figure 7A:
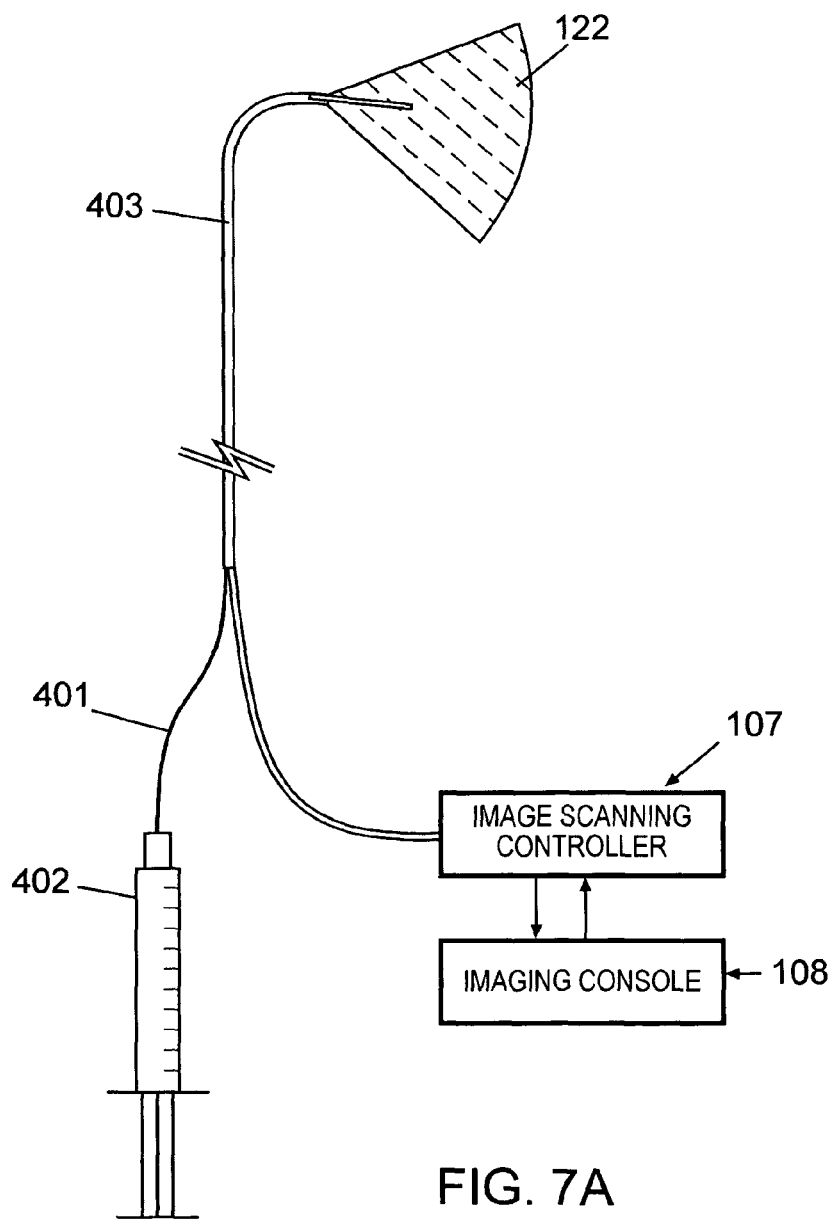

FIG. 7A shows a third manner in which a therapeutic catheter is adapted to include an image guidance mechanism. A catheter body 403 includes a needle 401 within a channel of the catheter body 403, whereby the needle 401 extends beyond the distal end of the catheter and into the field of view 122 of the imaging assembly 200. A syringe 402 or other injection mechanism can be connected to the lumen of the needle 401 either directly or via a port. As mentioned previously for the needle-carrying lumen of the device in FIG. 4A, advancement of a sharp needle tip through a needle-carrying lumen of a bendable device such as a polymer catheter can on occasion allow the needle tip to puncture through the body of the catheter and thus damage the mechanical integrity of the catheter system. For this reason, it may be desirable to construct the inner surface of all or a portion of a needle-carrying lumen with one or more materials that are resistant to needle puncture.

This embodiment of the catheter system in which the syringe is a reservoir for holding therapeutic/diagnostic agents may be used for delivery of these therapeutic/diagnostic agents to the target site. The therapeutic/diagnostic agents may include, but are not limited to medicaments, drugs, therapeutic agents, diagnostic agents, myocytes, myoblasts, cells, genetic material, gene therapy preparation, protein and imaging agents such as radiopaque dye.

FIG. 7B provides a higher detail view of a longitudinal cross-section of the distal end of the injection catheter with image guidance. The imaging assembly 120 has a field of view that includes the distal end of the needle 401 through an imaging window 106. Several applications exist for combined image guidance and injection, including chemical ablation, local drug delivery, stem cell injections and many others. By incorporating image guidance within a catheter body adapted to include a forward looking imaging assembly, the advantages of anatomic accuracy, reduced procedure times and lower complication rates become possible. Similarly, image guided aspiration can be accomplished via a needle incorporated with the present device.

Figure 8A:
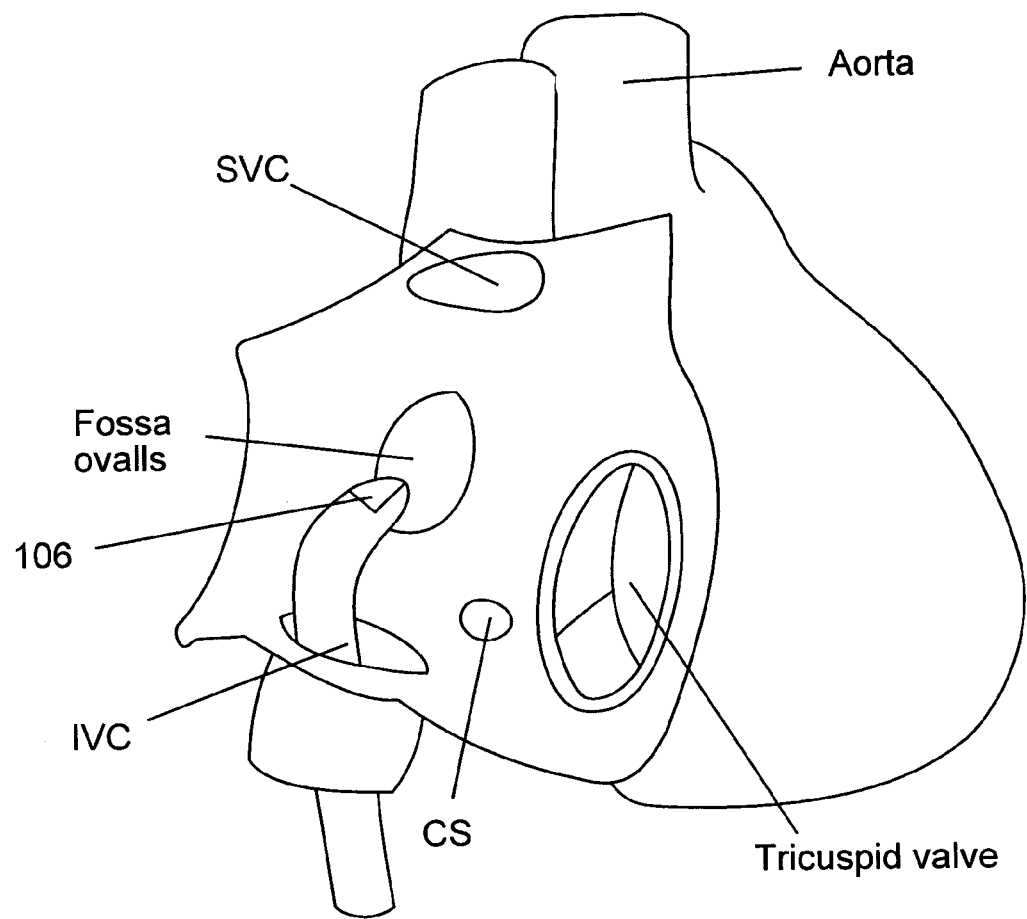
FIG. 8A shows deployment of the catheter into the right atrium via the inferior vena cava (IVC). The catheter tip, which contains the imaging apparatus, can be seen approaching the fossa ovalis in preparation for transseptal puncture. CS denotes coronary sinus, SVC denotes superior vena cava, IVC denotes inferior vena cava.

FIG. 8A shows the catheter inserted into the right atrium via the inferior vena cava (IVC). Alternatively the catheter can be inserted into the right atrium via the superior vena cava (SVC). The imaging window 106 is situated at the catheter tip and monitors the position of the catheter tip in relation to the fossa ovalis, which is the preferred location for septal puncture and transseptal approach to the left atrium. CS denotes coronary sinus.

Figure 8B:
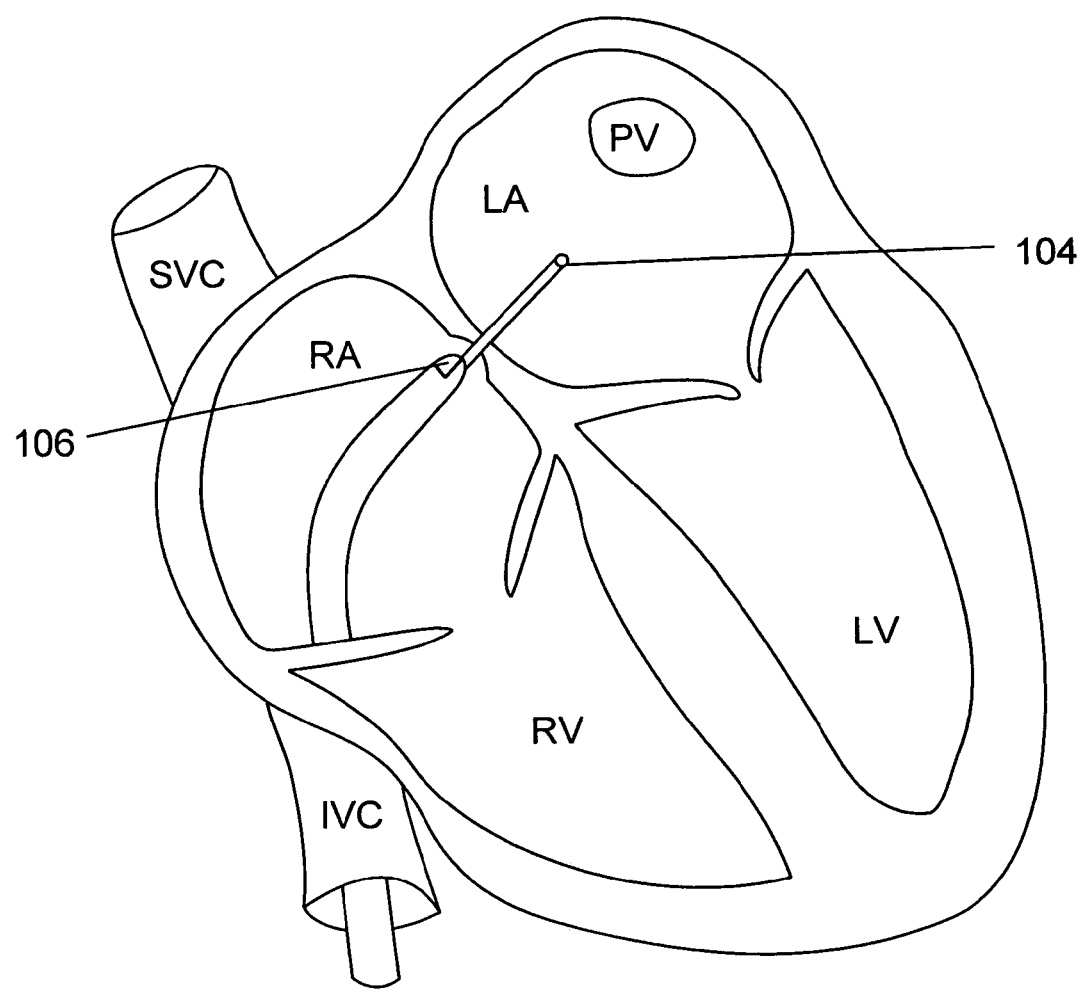
FIG. 8B shows a transseptal puncture via the fossa ovalis. The catheter tip with the imaging apparatus is situated within the right atrium adjacent to the fossa ovalis (FO), and the penetration needle tip lies within the left atrial cavity. IVC denotes inferior vena cava, SVC denotes superior vena cava, RA denotes right atrium, LA denotes left atrium, RV denotes right ventricle, LV denotes left ventricle, PV denotes pulmonary vein.

FIG. 8B shows transseptal penetration of the inter-atrial septum by a needle 104 under guidance from the imaging window 106 which is located within the catheter tip. The catheter tip is located within the right atrium, adjacent to the fossa ovalis, and the penetration needle tip is located within the left atrial cavity. IVC denotes inferior vena cava, SVC denotes superior vena cava, RA denotes right atrium, LA denotes left atrium, RV denotes right ventricle, LV denotes left ventricle, PV denotes pulmonary vein.

Figure 8C:
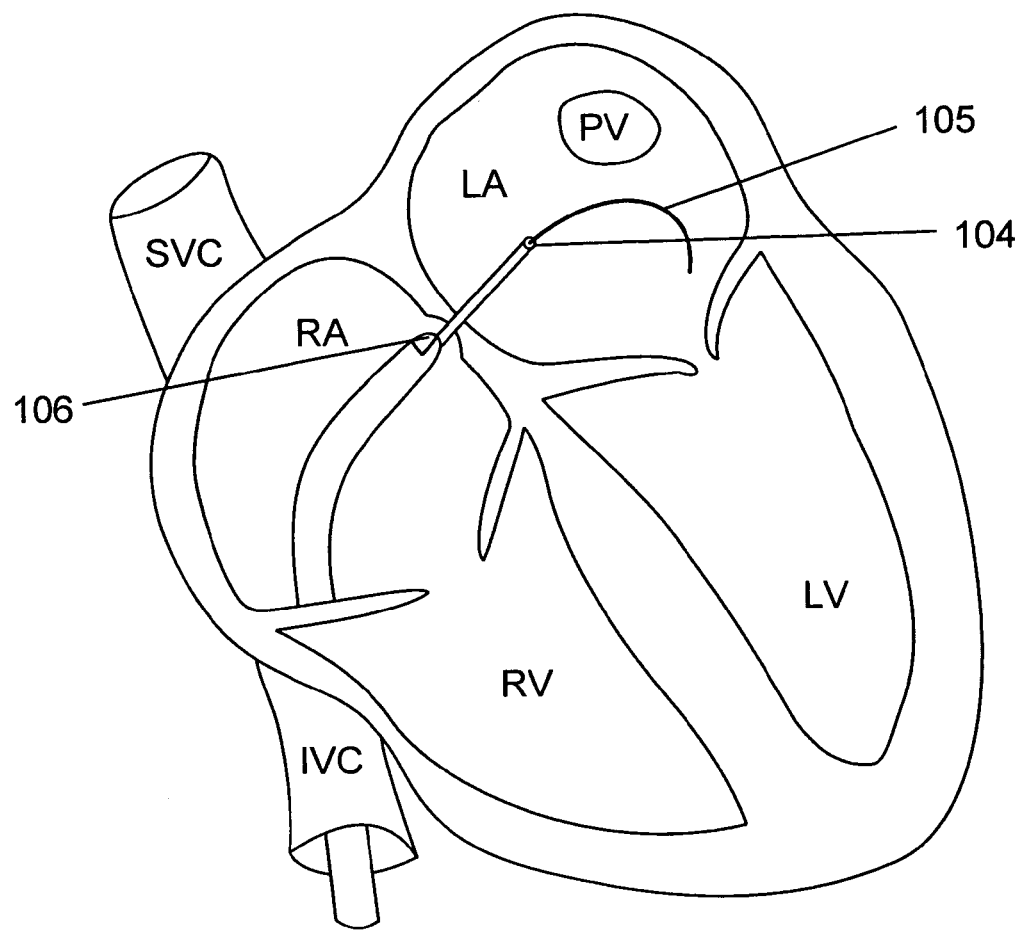
FIG. 8C shows advancement of a wire through the transseptal penetration needle. The imaging apparatus within the catheter tip, which is situated within the right atrium adjacent to the fossa ovalis, may monitor and guide advancement of the wire into the left atrial cavity. The wire may then serve as rail for transseptal insertion of specific diagnostic and therapeutic devices. IVC denotes inferior vena cava, SVC denotes superior vena cava, RA denotes right atrium, LA denotes left atrium, RV denotes right ventricle, LV denotes left ventricle, PV denotes pulmonary vein.

FIG. 8C shows insertion of a guidewire 105 through the penetration needle 104 within the left atrial cavity. This procedure may be guided by the imaging window 106, which is located within the right atrium, adjacent to the fossa ovalis. The guide wire may be used as a rail for transseptal insertion of various devices into the left atrial cavity, such as valvuloplasty balloons, prosthetic valves, and the catheter itself. IVC denotes inferior vena cava, SVC denotes superior vena cava, RA denotes right atrium, LA denotes left atrium, RV denotes right ventricle, LV denotes left ventricle, PV denotes pulmonary vein.

Figure 8D:
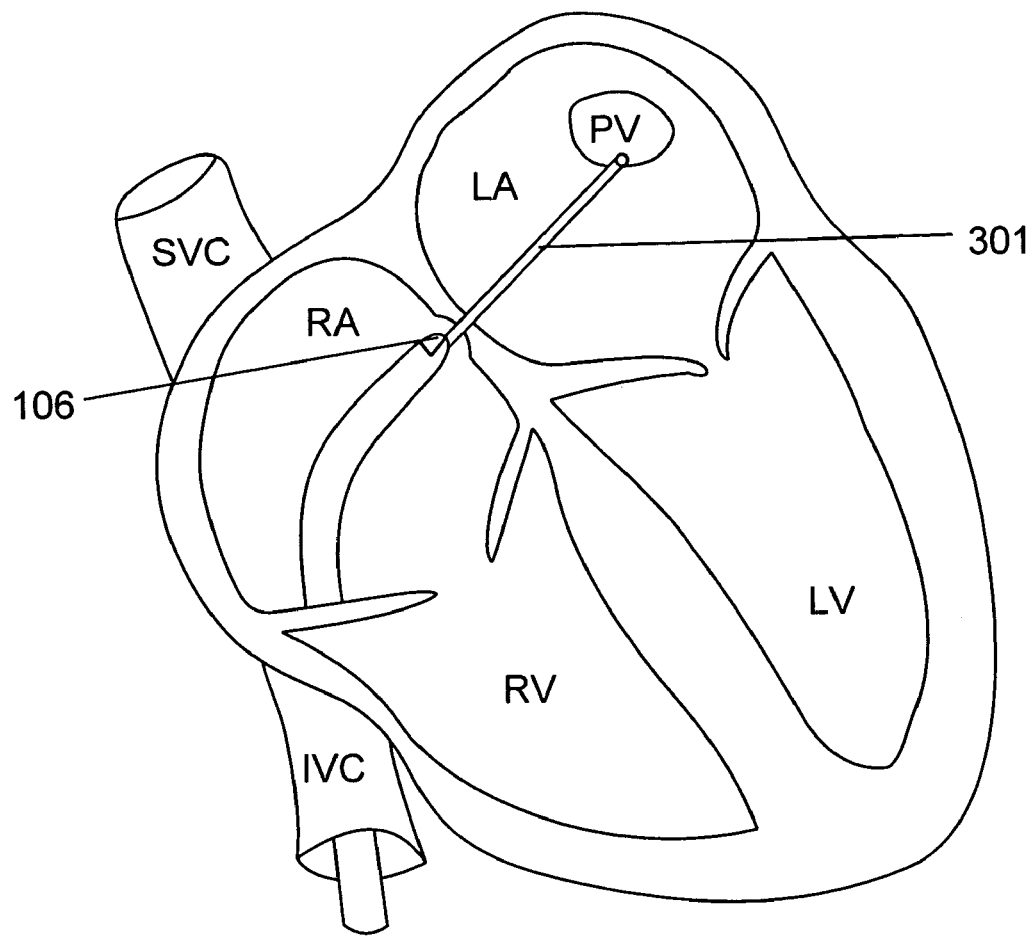
FIG. 8D shows transseptal advancement of an electrical conductor to the vicinity of the pulmonary veins for the purpose of ablation of atrial fibrillation. This procedure may be guided by the imaging apparatus within the catheter tip.

FIG. 8D shows transseptal insertion of an electrical conductor 301 from the right atrium into the left atrial cavity, in the vicinity of the pulmonary veins. The electrical conductor may be used to deliver electrical energy from for ablation of arrhythmia such as atrial fibrillation. The procedure may be guided by the imaging window 106, which is located within the right atrium, adjacent to the fossa ovalis. IVC denotes inferior vena cava, SVC denotes superior vena cava, RA denotes right atrium, LA denotes left atrium, RV denotes right ventricle, LV denotes left ventricle, PV denotes pulmonary vein.

Figure 8E:
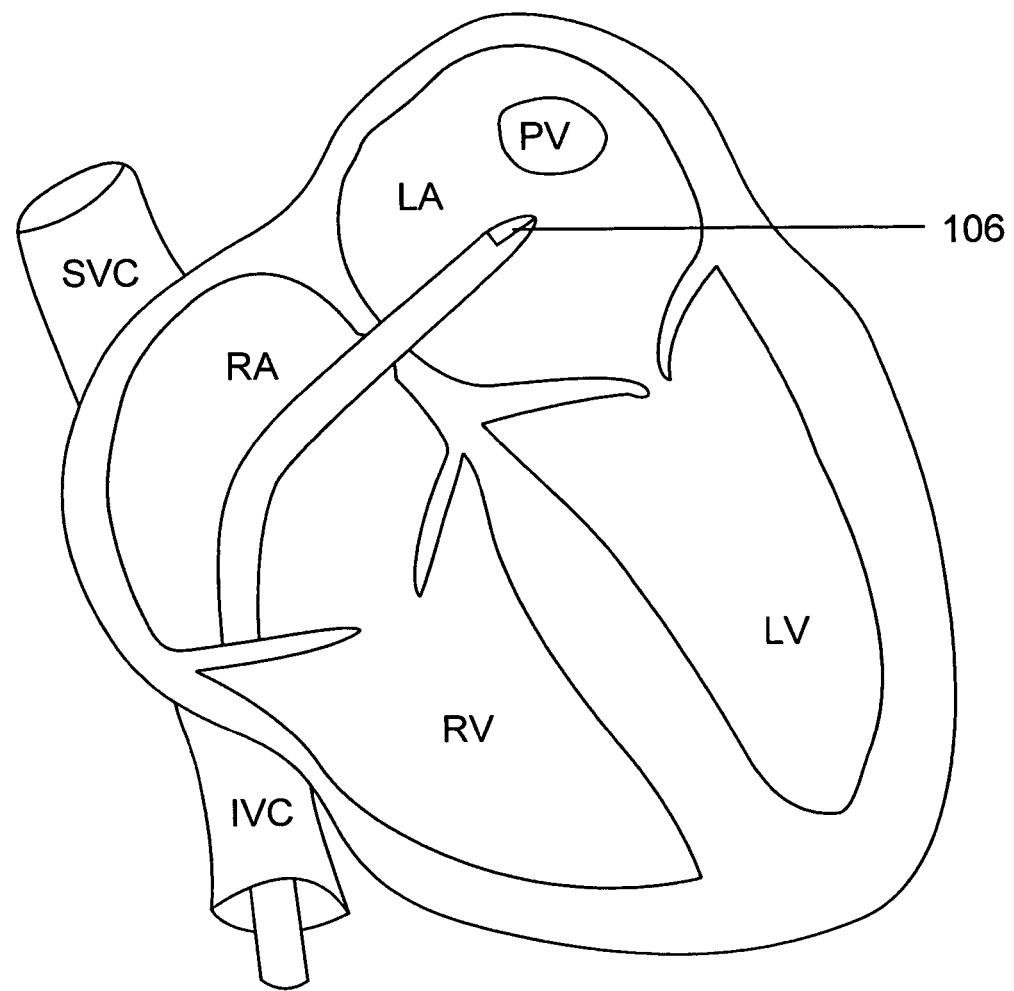
FIG. 8E shows transseptal advancement of the catheter containing the imaging apparatus from the right atrium into the left atrium.

FIG. 8E shows transseptal advancement of the catheter. The imaging window 106 may be positioned adjacent to the region of interest for guidance of specific interventions and diagnostic procedures. IVC denotes inferior vena cava, SVC denotes superior vena cava, RA denotes right atrium, LA denotes left atrium, RV denotes right ventricle, LV denotes left ventricle, PV denotes pulmonary vein.

FIG. 9 shows the schematic structure of an ablation catheter. An electrical conductor 301 will include one or more surface electrodes 304 near its distal end. There may be several conductors, each with one or more separate surface electrodes. The electrical conductor 301 will be positioned within a carrying lumen 111. The imaging assembly 120 will be contained with an outer sheath 101 and may have an imaging window incorporated at the distal end 114 of the outer sheath 101. The electrical conductor 301 and the surface electrode 304 will be advanced from within the carrying lumen 111 following penetration of the inner-atrial septum. Alternatively the one or more electrical conductors 301 and surface electrodes 304 will be employed to delived ablative energy in order to facilitate the transseptal puncture.

FIG. 10 shows the schematic structure of a biopsy catheter. A bioptome 600 will be positioned within a carrying lumen 111. The imaging assembly 120 will be contained with an outer sheath 101 and may have an imaging window incorporated at the distal end 114 of the outer sheath 101. The bioptome 600 will be advanced from within the carrying lumen 111.

Figure 11:
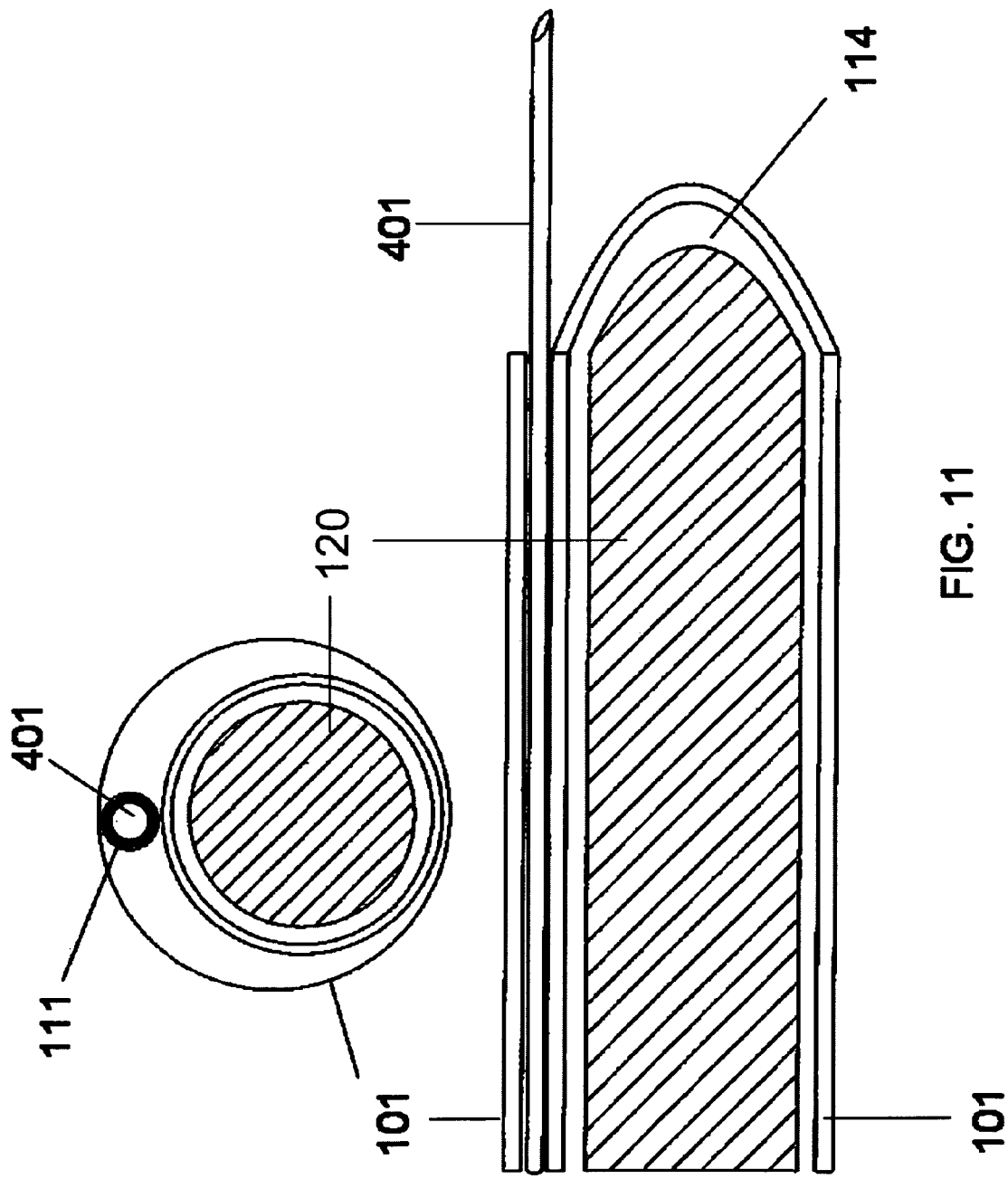
FIG. 11 shows the catheter outfitted with an injection needle.

FIG. 11 shows the schematic structure of an injection catheter. A needle 401 will be positioned within a carrying lumen 111. The imaging assembly 120 is contained with an outer sheath 101 and may have an imaging window incorporated at the distal end 114 of the outer sheath 101. The needle 401 is advanced from within the carrying lumen 111.

FIG. 12 shows the schematic structure of a penetration catheter containing a needle 104 through which a guide-wire 105 is inserted. The needle 104 can be positioned within a carrying lumen 111. The imaging assembly 120 will be contained with an outer sheath 101 and may have an imaging window incorporated at the distal end 114 of the outer sheath 101. The needle 104 will be advanced from within the carrying lumen 111 through the inter-atrial septum. The guidewire 105 is then inserted into the left atrial cavity and serves as a rail for transseptal insertion of specific diagnostic and therapeutic devices.

In addition, each of the preceding embodiments may be modified by including a mechanism for steering a length of the distal region of the catheter using steering mechanisms known in the art, such as that of Badger (U.S. Pat. Nos. 4,898,577 and 5,030,204) which are hereby incorporated by reference.

The present devices of the present invention are very advantageous since they provide the imaging and therapeutic apparatus in one integrated embodiment, thereby obviating the need for additional imaging devices. This may reduce costs as well as prevent incremental iatrogenic complications from invasive imaging.

The devices disclosed herein may be used for interventions in any fluid filled space in the body. Non-limiting examples include intervention in and through the inter-atrial septum, atrial fibrillation ablation, ablation of accessory pathways, occlusion of left atrial appendage, mitral valve interventions (eg. repair and valvuloplasty), aortic valve interventions (eg. prosthetic valve implantation and valvuloplasty), closure of atrial septal defects (ASD and PFO); intervention in and through the inter-ventricular septum, closure of a ventricular septal defect, ablation of accessory pathways; interventions within the cavity of the cardiac ventricles, intra-myocardial injection of genes, cells, medications, agents, direct myocardial revascularization, myocardial biopsy; interventions within the coronary sinus; creation of fenestrations through aortic stent-grafts; urological procedures; treatment of elevated intracranial pressure; gynecological procedures; creation of arterial-venous connections (fistulae); percutaneous coronary artery bypass interventions; and creation of hemodialysis shunts. These interventions are discussed in more detail herebelow.

1) Transseptal Puncture and Interventions

See in the Background section.

2) Intervention in and Through the Inter-Ventricular Septum

Congenital ventricular septal defect (VSD) is usually detected and treated during childhood. Acquired VSD is a serious complication of myocardial infarction and may also develop following cardiac trauma. Open heart surgery is the standard treatment for VSD. Percutaneous closure of VSD may be performed in some patients in whom the surgical risk is prohibitive. This complex procedure is performed under fluoroscopic and echocardiographic guidance (see Heart Lung Circ. 2008; 17(2):119-23. Percutaneous closure of post-myocardial infarction ventricular septal defects: a single centre experience. Ahmed J, Ruygrok P N, Wilson N J, Webster M W, Greaves S, Gerber I), however these imaging modalities are not optimal for detecting and accurately delineating the defect. The proposed embodiment would include a catheter with forward-looking imaging at its tip which through which a closure device would be positioned in the VSD.

3) Interventions Within the Cavity of the Cardiac Ventricles

A variety of diagnostic procedures and therapeutic interventions are performed within the left and right cardiac ventricles. Myocardial biopsy is a procedure during which a small portion of tissue is removed from the heart muscle for testing. This procedure usually performed within the right ventricle under fluoroscopic guidance. The biopsy must be obtained from the interventricular septum and not from the thin-walled free wall in order to prevent potentially fatal cardiac perforation, however fluoroscopy is limited in its ability to accurately define the specific location in which the biopsy is being performed. The present embodiment would include a forward-looking myocardial biopsy device which would be inserted from a peripheral vein through the right atrium into the right ventricle. The forward-looking imaging device at the catheter tip would ensure accurate and safe localization of the desired anatomical site for biopsy.

Targeted endomyocardial injection of cells, genes, medications and proteins is an evolving field which may potentially be used for treatment of a variety of cardiac disorders. Accurate localization of the injection target is vital. Fluoroscopy is limited in its ability to image cardiac tissue and navigate catheters and injection devices within the ventricular cavity, and is therefore unreliable for guidance of endomyocardial injections. Magnetic resonance imaging has been used to guide endomyocardial imaging (see Circulation. 2002 19; 105(11):1282-4. Catheter-based endomyocardial injection with real-time magnetic resonance imaging. Lederman R J, Guttman M A, Peters D C, Thompson R B, Sorger J M, Dick A J, Raman V K, McVeigh E R), however this imaging is limited by expense, limited availability and incompatibility with ferro-magnetic implants. Electromechanical mapping (NOGA, Biosense Webster) can also be used to guide endomyocardial injection (see J Am Coll Cardiol. 2003 Dec. 17; 42(12):2063-9. Catheter-based intramyocardial injection of autologous skeletal myoblasts as a primary treatment of ischemic heart failure: clinical experience with six-month follow-up. Smits P C, van Geuns R J, Poldermans D, Bountioukos M, Onderwater E E, Lee C H, Maat A P, Serruys P W) however this technique has limited availability and does not directly image the injected tissue. The present embodiment would include a catheter with forward-looking imaging at its tip and an injection needle. An iteration of this device would include a laser source at the catheter tip for performance of direct myocardial revascularization by drilling holes from within the ventricular cavity into the myocardial tissue.

4) Interventions Within the Coronary Sinus

Coronary sinus catheterization is required for a variety of diagnostic procedures and therapeutic interventions which include sampling of venous blood (see Eur Heart J. 2007 April; 28(8):929-40. Coronary sinus blood sampling: an insight into local cardiac pathophysiology and treatment? Jaumdally R, Varma C, Macfadyen R J, Lip G Y.), implantation of pacemaker electrodes (see Circulation. 2007 Apr. 24; 115(16):2208-20. Interventional electrophysiology and cardiac resynchronization therapy: delivering electrical therapies for heart failure. Burkhardt J D, Wilkoff B L), implantation of devices for treatment of mitral regurgitation (see Circulation. 2008 Feb. 19; 117(7):963-74. Evolving concepts and technologies in mitral valve repair. Fedak P W, McCarthy P M, Bonow R O), implantation of a coronary sinus reducer for treatment of chronic refractory angina pectoris (see J Am Coll Cardiol. 2007 May 1; 49(17): 1783-9. Coronary sinus reducer stent for the treatment of chronic refractory angina pectoris: a prospective, open-label, multicenter, safety feasibility first-in-man study. The anatomy of the right atrium and coronary sinus is variable and may be distorted in the presence of heart disease. The present embodiment would consist of a catheter with forward-looking imaging for observation of the coronary sinus, through which the required procedures may be performed.

5) Creation of Fenestrations Through Aortic Stent-Grafts

Aortic stent grafting is an endovascular treatment for diseases of the aorta, including aortic aneurysm and aortic dissection. This treatment spares the patients the need to undergo open vascular surgery which is associated with significant morbidity and mortality. One limitation of this approach is that the stent graft may occlude side-branches of the aorta, thereby causing acute ischemia in the subtended tissue (see J Vasc Surg. 2007 January; 45(1):90-4. Coverage of the left subclavian artery during thoracic endovascular aortic repair. Riesenman P J, Farber M A, Mendes R R, Marston W A, Fulton J J, Keagy B A). This complication may be avoided or treated by creating fenestrations within the stent graft in order to reperfuse the occluded side-branches. The fenestration procedure needs to be accurately guided in order to correctly position the fenestrations so that the side-branches are reperfused and no trauma is inflicted upon the aortic wall or stent graft itself. Fluoroscopic guidance is limited in its ability detect accurately locate the three-dimensional geometry of the aorta and its arterial branches. The present embodiment would incorporate forward-looking imaging at the catheter tip in order to accurately define the trajectory of the fenestration needle through the membrane of the aortic stent-graft into the target blood vessel beyond it. More generally, such an approach can be applied to creating fenestrations in any prosthetic conduit, such as aortic stent-grafts.

6) Urological Procedures

Endoscopy of the urinary tract is usually performed with a catheter which is guided by optical fibers that convey the image from the catheter tip. These catheters may be used to view the intraluminal surface anatomy of the urethra, urinary bladder and ureters. Under certain conditions it may be desirable to view the underlying structure of observed anatomy beyond the observable surface. The present embodiment would be comprised of an endoscopic catheter with forward-looking imaging at its tip. This catheter would be used for diagnostic purposes for observation of the luminal surface of the urinary tract and also for guidance of interventions such as biopsies and retrieval of renal calculi (kidney stones).

7) Intracranial Procedures

Blockage of cerebrospinal fluid (CSF) pathways within the brain may cause increased intracranial pressure leading to hydrocephalus and brain damage. The conventional treatment for obstruction of CSF pathways is by creation of a surgical shunt, however the long-term outcome of these operations is dismal due to shunt blockage and infections. Recently, endoscopic treatment of CSF pathway obstruction has been performed, including such procedures as septum pellucidum fenestration, third ventriculostomy, lamina terminalis fenestration, temporal ventriculostomy, aqueductoplasty, aqueductal stenting and foraminoplasty of the foramen of Monro. These procedures are performed through endoscopes that are inserted into the brain through small holes drilled through the skull. Optically guided endoscopes are used as platforms for insertion of a variety of instruments including scissors, hooks, puncture needles, biopsy and grasping forceps, balloon catheters and stents. Sometimes optical orientation of the endoscope is difficult because of lack of anatomical landmarks, and intraoperative ultrasound imaging is helpful (see Neurosurgery. 2007 February; 60(2 Suppl 1):ONS44-51. Endoscopic treatment of cerebrospinal fluid pathway obstructions. Schroeder H W, Oertel J, Gaab M R). The present embodiment would include an endoscope with forward-looking imaging and a lumen for insertion of the desired interventional tools for performance of endoscopic treatment of CSF pathway obstruction.

8) Gynecological Interventions

A variety of minimally invasive techniques have been developed to diagnose and treat disorders of the female genital tract and infertility. These endoscopic techniques are alternatives to open or laparscopic surgery which is a more invasive approach. Hysteroscopy is an endoscopic technique for observing, diagnosing and treating pathological conditions of the uterine cavity (see J Minim Invasive Gynecol. 2007 July-August; 14(4):407-18. Development of hysteroscopy: from a dream to a reality, and its linkage to the present and future. Valle R F) and salpingoscopy is a technique for viewing and performing procedures in the fallopian tubes (see Curr Opin Obstet Gynecol. 2004 August; 16(4):325-9. The role of selective salpingography and tubal catheterization in the management of the infertile couple. Papaioannou S, Afnan M, Sharif K.). These procedures are performed under x-ray or optical guidance however these methods have certain limitations. X-ray exposure is undesirable in fertile females as radiation may cause congenital malformations. Optical guidance is limited in its ability to visualize beyond an obstruction within the female genital tract or to assess the inner structure of observed pathologies such masses within the tract. The present embodiment would include an endoscope with forward-looking imaging and a lumen for insertion of diagnostic and therapeutic devices.

Thus, in summary, an embodiment of the present invention is comprised of a catheter and needle for transseptal puncture, which incorporates a forward-looking ultrasound imaging mechanism near the catheter tip. The wiring of the ultrasound system runs distally in a separate lumen back to hub of the catheter, where it connects to an ultrasound console (echocardiography or intravascular ultrasound) and may optionally be connected in a manner to be displayed on a panel next to the fluoroscopy screen in the catheterization laboratory.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An elongate catheter having a proximal end and a distal end, wherein said elongate catheter is insertable, distal end first, into a natural or human-made lumen or cavity within the body of a mammalian patient, said elongate catheter comprising:
    a medical device with a functional component near said distal end of said elongate catheter, wherein said medical device is advanceable to a target location in the vicinity of said distal end of said elongate catheter; and
    an imaging probe having a rotatable shaft and a forward-looking imaging assembly, wherein said imaging assembly is attached to said rotatable shaft, wherein said imaging assembly is positionable near said distal end of said elongate catheter, said imaging assembly including a scanning mechanism, wherein said imaging assembly is configured to scan a field of view for determining a position of the target location within the patient's body relative to a trajectory on which said medical device will advance such that an image angle of said scanning mechanism may be varied by adjusting the rotational velocity of said rotatable shaft.

2. The elongate catheter according to claim 1 further comprising an imaging probe receiving lumen, wherein said imaging probe is insertable into said imaging probe receiving lumen.

3. The elongate catheter according to claim 1 wherein said medical device is an interventional medical device.

4. The elongate catheter according to claim 3 wherein said interventional medical device is selected from the group consisting of: tissue penetrators, dilators, needles, wires, balloons, stents, electrodes, laser energy sources, occluders, closure devices, prosthetic valves, valve repair devices, prosthetic tubing, and injection apparatus.

5. The elongate catheter according to claim 3 wherein said interventional medical device includes a hollow needle enclosing a passageway therethrough.

6. The elongate catheter according to claim 5 wherein said interventional medical device further comprises a wire that is insertable through the hollow needle.

7. The elongate catheter according to claim 5 including a reservoir in flow communication with said passageway for storing agents to be delivered to the target location.

8. The elongate catheter according to claim 7 wherein said agents stored in said reservoir are selected from the group consisting of: medicaments, drugs, therapeutic agents, diagnostic agents, myocytes, myoblasts, cells, genetic material, gene therapy preparation, protein, dye, and radiopaque material.

9. The elongate catheter according to claim 1 wherein said medical device is a diagnostic medical device.

10. The elongate catheter according to claim 9 wherein said diagnostic medical device is selected from the group consisting of: probes, electrodes, electronic sensors, biopsy apparatus, aspiration apparatus, optical coherence tomography imaging, and ultrasound imaging.

11. A dilating catheter for dilating a tissue of a mammalian patient, comprising:
    a dilator having a proximal end and a distal end, said dilator being insertable, distal end first, into a natural or human made lumen or cavity within the body of a mammalian patient; and
    an imaging assembly mounted within said distal end of said dilator, the imaging assembly being capable of imaging a region of interest near said distal end of said dilator;
    wherein a distal portion of said dilator includes a transmissive window allowing transmission of imaging energy between the imaging assembly and the region of interest.

12. The dilating catheter according to claim 11 wherein the imaging assembly is configured for one or more of emitting ultrasound energy and receiving ultrasound energy.

13. The dilating catheter according to claim 11 wherein the imaging assembly is configured for one or more of emitting optical energy and receiving optical energy.

14. The dilating catheter according to claim 13 wherein the imaging assembly is configured for optical coherence tomography imaging.

15. The dilating catheter according to claim 11 wherein said dilator includes a needle-carrying lumen.

16. The dilating catheter according to claim 11 further comprising a tissue penetration mechanism near said distal end of said dilator, wherein said tissue penetration mechanism is advanceable to a target location in the vicinity of said distal end of said dilator.

17. The dilating catheter according to claim 11 wherein said distal end of said dilator is shaped for dilating tissue of a cardiac septum.

18. The dilating catheter according to claim 11 wherein said distal end of said dilator is shaped for dilating tissue of an atrial septum.

19. The dilating catheter according to claim 12 wherein the imaging energy is a combination of both ultrasound energy and optical energy, and wherein the optical energy is of suitable wavelength and amplitude for optical coherence tomography imaging.

20. A method for delivering a medical device to a target location within the body of a mammalian patient, comprising the steps of:
(a) providing an elongate catheter having a proximal end and a distal end, wherein the elongate catheter is insertable, distal end first, into a natural or human-made lumen or cavity within the body of the mammalian patient, the elongate catheter comprising:
a medical device with a functional component near the distal end of the elongate catheter, wherein the medical device is advanceable to the target location in the vicinity of the distal end of the elongate catheter; and
an imaging probe having a rotatable shaft and a forward-looking imaging assembly, wherein the imaging assembly is attached to the rotatable shaft, wherein the imaging assembly is positionable near the distal end of the elongate catheter, the imaging assembly including a scanning mechanism, wherein the imaging assembly is configured to scan a field of view for determining a position of the target location within the mammalian patient's body relative to a trajectory on which the medical device will advance such that an image angle of said scanning mechanism may be varied by adjusting the rotational velocity of the rotatable shaft; and
biasing means for biasing the medical device into the field of view of the imaging assembly such that when the medical device is subsequently advanced, the medical device will enter the target location in the field of view;
(b) inserting the elongate catheter into the natural or human-made lumen or cavity within the body of the mammalian patient;
(c) adjusting to rotational velocity of the rotatable shaft and obtaining an image within the field of view of the imaging probe;
(d) determining, using the image, the position of the target location within the mammalian patient's body relative to the trajectory on which the medical device is advanceable;
(e) adjusting, if necessary, one or more of a position and rotational orientation of the elongate catheter within the natural or human-made lumen such that when the medical device is advanced, the medical device enters the target location in the field of view of the imaging probe; and
(f) advancing the medical device from the elongate catheter to the target location.

21. The method according to claim 20 wherein the medical device is selected from the group consisting of: interventional medical device and diagnostic medical device.

22. The method according to claim 21 wherein the natural or human-made lumen or cavity within the body of the mammalian patient is a first blood vessel.

23. The method according to claim 22 wherein the target location is a second lumen of a second blood vessel adjacent to the first blood vessel.

24. The method according to claim 20 wherein the natural or human-made lumen within the body of the mammalian patient is a human-made lumen that has been created within, or outside of, the wall of an adjacent anatomical conduit; the wall of the anatomical conduit defining a lumen of the anatomical conduit; and wherein the target location is the lumen of the anatomical conduit.

25. The method according to claim 24 wherein the anatomical conduit is a blood vessel.

26. The method according to claim 20 wherein the medical device has a lumen extending therethrough.

27. The method according to claim 26 wherein, prior to or concurrently with performing step (e), the method further comprises the step of advancing an apparatus through the lumen of the medical device and to the target location.

28. The method according to claim 27 wherein the apparatus that is advanced through the lumen of the medical device and to the target location is selected from the group consisting of: guidewire, electrode, sensor, transponder, transmitter, receiver apparatus for delivering therapy, drug delivery apparatus, catheter, dilator, needle, wire, balloon, stent, laser energy source, occluder, closure device, prosthetic valve, valve repair device, prosthetic conduit, and injection apparatus.

29. The method according to claim 28 wherein, subsequent to performing the step of advancing the apparatus through the lumen of the medical device and to the target location, the method further comprises a step of withdrawing the medical device into the catheter while leaving the apparatus in place at the target location.

30. The method according to claim 26 wherein the method further comprises the step of delivering a substance through the lumen of the medical device.

31. The method according to claim 30 wherein the substance delivered through the lumen of the medical device is selected from the group consisting of: medicament, drug, therapeutic agent, diagnostic agent, myocytes, myoblasts, other cells, genetic material, gene therapy preparation, protein, dye and radiopaque material.

32. The method according to claim 26 wherein the method further comprises the step of advancing a guidewire through the lumen of the medical device and subsequently advancing another apparatus over the guidewire to the target location.

33. The method according to claim 26 wherein the method further comprises the step of advancing a second catheter through the lumen of the medical device and subsequently delivering a substance or apparatus through the second catheter to the target location.

34. The elongate catheter according to claim 1 further comprising a biasing means for biasing said medical device into the field of view of said imaging assembly such that when said medical device is subsequently advanced, said medical device will enter the target location in the field of view.

35. The dilating catheter according to claim 16 wherein said tissue penetration mechanism includes one or more electrical conductors connected to one or more surface electrodes, wherein the electrical conductors are configured to facilitate puncture through the tissue by ablation.

36. The method according to claim 20 wherein the medical device includes a tissue penetration mechanism, wherein the tissue penetration mechanism is advanceable to the target, and wherein the method further comprises the step of:
f) penetrating the tissue at the target location with the tissue penetration mechanism.

37. The method according to claim 36 wherein the elongate catheter further includes a dilator, wherein a distal portion of the dilator is shaped for dilation of the tissue after the tissue has been penetrated, and wherein the method further comprises the step of:

g) advancing the elongate catheter such that the dilator dilates the tissue at the target location, thereby producing a dilated hole in the tissue.

38. The method according to claim 37 further comprising the step of advancing a portion of the elongate catheter through the dilated hole.

39. The method according to claim 20 wherein the natural or human-made lumen or cavity within the body of the mammalian patient is a cardiac chamber.

40. The method according to claim 39 wherein the target location is the fossa ovalis.

* * * * *

UNITED STATES PATENT AND TRADEMARK OFFICE
CERTIFICATE OF CORRECTION

PATENT NO. : 8,172,757 B2
APPLICATION NO. : 12/213386
DATED : May 8, 2012
INVENTOR(S) : Ronen Jaffe et al.

It is certified that error appears in the above-identified patent and that said Letters Patent is hereby corrected as shown below:

Title Page, Item 54 and Column 1, replace application title "METHODS AND DEVICES FOR IMAGE-GUIDED MANIPULATION OR SENSING OR ANATOMIC STRUCTURES" to read --METHODS AND DEVICES FOR IMAGE-GUIDED MANIPULATION OR SENSING OF ANATOMIC STRUCTURES--.

Column 21, Claim 19, replace claim identifier [[12]] with --claim 11--.

Signed and Sealed this
Nineteenth Day of March, 2013

Teresa Stanek Rea
*Acting Director of the United States Patent and Trademark Office*